US012796999B2

(12) United States Patent
Sugahara et al.

(10) Patent No.: US 12,796,999 B2
(45) Date of Patent: Nov. 17, 2026

(54) INFORMATION PROVIDING DEVICE, INFORMATION PROVIDING METHOD, AND COMPUTER-READABLE STORAGE MEDIUM

(71) Applicant: JVCKENWOOD Corporation, Yokohama (JP)

(72) Inventors: Takayuki Sugahara, Yokohama (JP); Hayato Nakao, Yokohama (JP); Motomu Takada, Yokohama (JP); Hideo Tsuru, Yokohama (JP); Tetsuya Suwa, Yokohama (JP); Shohei Odan, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 692 days.

(21) Appl. No.: 18/179,409

(22) Filed: Mar. 7, 2023

(65) Prior Publication Data

US 2023/0200711 A1 Jun. 29, 2023

Related U.S. Application Data

(63) Continuation of application No. PCT/JP2021/034398, filed on Sep. 17, 2021.

(30) Foreign Application Priority Data

Sep. 18, 2020 (JP) ................................ 2020-157524
Sep. 18, 2020 (JP) ................................ 2020-157525
Sep. 18, 2020 (JP) ................................ 2020-157526

(51) Int. Cl.
*A61B 5/378* (2021.01)
*A61B 5/38* (2021.01)

(52) U.S. Cl.
CPC ................ *A61B 5/378* (2021.01); *A61B 5/38* (2021.01)

(58) Field of Classification Search
CPC ......... A61B 5/378; A61B 5/38; A61B 5/0205; A61B 5/1112; A61B 5/1116;
(Continued)

(56) References Cited

U.S. PATENT DOCUMENTS 6,212,502 B1 * 4/2001 Ball ........................ G10L 17/26 704/275
11,709,550 B2 * 7/2023 Yokoyama ............. G06F 3/014 715/702

(Continued)

FOREIGN PATENT DOCUMENTS

JP 2011-096171 5/2011
JP 2011-242219 12/2011

(Continued)

OTHER PUBLICATIONS

International Search Report and Written Opinion for International Application No. PCT/JP2021/034398 mailed on Nov. 2, 2021, 9 pages.

*Primary Examiner* — Bryan Earles
(74) *Attorney, Agent, or Firm* — Amin, Turocy & Watson, LLP

(57) ABSTRACT

An information providing device includes a display unit configured to output a visual stimulus; a sound output unit configured to output an auditory stimulus; a sensory stimulus output unit configured to output a sensory stimulus; an environment sensor configured to detect position information of the information providing device; a biological sensor configured to detect cerebral activation degree of a user; an output selecting unit configured to select, based on the environment information, one of the display unit, the sound output unit, and the sensory stimulus output unit; an output (Continued)

specification deciding unit configured to decide on a reference output specification for adjusting outputs of the display unit, the sound output unit, and the sensory stimulus output unit, based on the position information; and a user state identifying unit configured to calculate an output specification correction degree for correcting the reference output specification, based on the cerebral activation degree.

13 Claims, 11 Drawing Sheets

(58) Field of Classification Search
CPC .......... A61B 5/6803; G06F 3/01; G09G 5/00; G09G 5/36; G09G 5/377
See application file for complete search history.

(56) References Cited

U.S. PATENT DOCUMENTS

| | | | | |
|---|---|---|---|---|
| 11,948,256 | B2 * | 4/2024 | Rabinovich | G06F 1/163 |
| 2016/0077547 | A1 * | 3/2016 | Aimone | A61B 3/113 345/8 |
| 2017/0102765 | A1 * | 4/2017 | Yoneda | G06Q 30/0269 |
| 2017/0162177 | A1 * | 6/2017 | Lebeck | G06F 21/6218 |
| 2017/0323161 | A1 * | 11/2017 | Du | G06V 40/174 |
| 2019/0035124 | A1 * | 1/2019 | Kapinos | G06T 11/60 |
| 2021/0145340 | A1 * | 5/2021 | Asukai | A61B 5/0077 |

FOREIGN PATENT DOCUMENTS

| | | |
|---|---|---|
| JP | 2019-082952 | 5/2019 |
| JP | 2020-009027 | 1/2020 |
| JP | 2020-067693 | 4/2020 |
| WO | 2019/207896 | 10/2019 |

* cited by examiner

FIG.5

ENVIRONMENT SCORE

| CATEGORY | SUB-CATEGORY | ENVIRONMENT SENSOR | ENVIRONMENT D1 | ENVIRONMENT D2 | ENVIRONMENT D3 | ENVIRONMENT D4 |
|---|---|---|---|---|---|---|
| POSTURE | STANDING STATE | CAMERA | 10 | 10 | 0 | 0 |
| | FACE ORIENTATION BEING IN HORIZONTAL DIRECTION | GYRO SENSOR | 100 | 90 | 90 | 90 |
| LOCATION | INSIDE TRAIN CAR | CAMERA | 90 | 0 | 5 | 20 |
| | ON RAILWAY TRACKS | GNSS RECEIVER | 100 | 0 | 0 | 0 |
| | SOUND INSIDE TRAIN CAR | MICROPHONE | 90 | 10 | 5 | 5 |
| MOVEMENT | MOVING | ACCELERATION SENSOR | 100 | 100 | 100 | 80 |
| SAFETY | BRIGHT | LIGHT SENSOR | 50 | 100 | 10 | 70 |
| | INFRARED LIGHT/ULTRAVIOLET LIGHT AT APPROPRIATE LEVEL | LIGHT SENSOR | 100 | 80 | 100 | 100 |
| | APPROPRIATE TEMPERATURE | TEMPERATURE SENSOR | 100 | 100 | 80 | 100 |
| | APPROPRIATE HUMIDITY | HUMIDITY SENSOR | 100 | 100 | 75 | 90 |
| | HAZARDOUS OBJECT PRESENT | CAMERA | 10 | 10 | 90 | 10 |
| | | MICROPHONE | 20 | 20 | 80 | 20 |

FIG.6

ENVIRONMENT PATTERN

| | ENVIRONMENT D1 | ENVIRONMENT D2 | ENVIRONMENT D3 | ENVIRONMENT D4 |
|---|---|---|---|---|
| ENVIRONMENT PATTERN | PT1 | PT2 | PT3 | PT4 |
| REMARKS | BEING SEATED IN TRAIN CAR | WALKING ON SIDEWALK | WALKING ON DARK SIDEWALK | SHOPPING |

FIG.8

TARGET DEVICE, REFERENCE OUTPUT SPECIFICATION

| ENVIRONMENT PATTERN | DISPLAY UNIT | SOUND OUTPUT UNIT | SENSORY STIMULUS OUTPUT UNIT | REMARKS |
|---|---|---|---|---|
| PT1 | LEVEL 4 | LEVEL 4 | LEVEL 4 | BEING SEATED IN TRAIN CAR |
| PT2 | LEVEL 3 | LEVEL 3 | LEVEL 3 | WALKING ON SIDEWALK |
| PT3 | LEVEL 0 | LEVEL 2 | LEVEL 2 | WALKING ON DARK SIDEWALK |
| PT4 | LEVEL 2 | LEVEL 2 | LEVEL 2 | SHOPPING |

FIG.10

OUTPUT SPECIFICATION CORRECTION DEGREE

| USER STATE | DEGREE | DISPLAY UNIT | SOUND OUTPUT UNIT | SENSORY STIMULUS OUTPUT UNIT |
|---|---|---|---|---|
| CEREBRAL ACTIVATION DEGREE | VA3 (LARGE) | -1 | -1 | -1 |
| | VA2 (MEDIUM) | 0 | 0 | 0 |
| | VA1 (SMALL) | 1 | 1 | 1 |
| MENTAL BALANCE DEGREE | VB3 (LARGE) | 1 | 1 | 1 |
| | VB2 (MEDIUM) | 0 | 0 | 0 |
| | VB1 (SMALL) | -1 | -1 | -1 |

FIG.11

OUTPUT RESTRICTION NECESSITY INFORMATION

| SENSOR/ ENVIRONMENT INFORMATION | GNSS RECEIVER/ SCORE FOR "ON RAILWAY TRACK" IS 100 | ACCELERATION SENSOR/ SCORE IS 0 |
|---|---|---|
| CEREBRAL ACTIVATION DEGREE VA3 (LARGE) | NON-AUTHORIZATION FOR USING DISPLAY UNIT | NON-AUTHORIZATION FOR USING DISPLAY UNIT |
| CEREBRAL ACTIVATION DEGREE VA2 (MEDIUM) | NON-AUTHORIZATION FOR USING DISPLAY UNIT | NON-AUTHORIZATION FOR USING DISPLAY UNIT |
| CEREBRAL ACTIVATION DEGREE VA1 (SMALL) | AUTHORIZATION FOR USING DISPLAY UNIT | AUTHORIZATION FOR USING DISPLAY UNIT |

INFORMATION PROVIDING DEVICE, INFORMATION PROVIDING METHOD, AND COMPUTER-READABLE STORAGE MEDIUM

CROSS-REFERENCE TO RELATED APPLICATION

This application is a Continuation of PCT International Application No. PCT/JP2021/034398 filed on Sep. 17, 2021 which claims the benefit of priority from Japanese Patent Applications No. 2020-157524, No. 2020-157525 and No. 2020-157526, filed on Sep. 18, 2020, the entire contents of all of which are incorporated herein by reference.

BACKGROUND

The present disclosure relates to an information providing device, an information providing method, and a computer-readable storage medium.

In recent times, information devices have been undergoing significant evolution due to high-speed CPUs, due to the high-definition screen display technology, accompanying the advancement in the technology of compact and lightweight batteries, and accompanying the prevalence of wireless network environments and widening of their bandwidth. As far as such information devices are concerned, along with the popularization of smartphones that represent a typical example, what are called wearable devices that are worn by the users have also become popular. For example, in Japanese Patent Application Laid-open No. 2011-96171, a device is disclosed that presents a plurality of sets of sensory information to the user, and gives the user the sense that virtual objects actually exist. In Japanese Patent Application Laid-open No. 2011-242219, regarding an information providing device, the providing form and the providing timing is decided in such a way that the sum of an evaluation function, which indicates the appropriateness level of the information providing timing, becomes equal to the maximum level.

Regarding an information providing device that provides information to a user, there has been a demand that the information is provided to the user in an appropriate manner.

SUMMARY

An information providing device according to an embodiment provides information to a user, and include: an output unit including a display unit configured to output a visual stimulus, a sound output unit configured to output an auditory stimulus, and a sensory stimulus output unit configured to output a sensory stimulus other than the visual stimulus and the auditory stimulus; an environment sensor configured to detect, as environment information surrounding the information providing device, position information of the information providing device; a biological sensor configured to detect, as biological information of the user, cerebral activation degree of the user; an output selecting unit configured to select, based on the environment information, one of the display unit, the sound output unit, and the sensory stimulus output unit; an output specification deciding unit configured to decide on a reference output specification for adjusting outputs of the display unit, the sound output unit, and the sensory stimulus output unit, based on the position information of the information providing device; and a user state identifying unit configured to calculate an output specification correction degree for correcting the reference output specification, based on the cerebral activation degree of the user. The output specification deciding unit is configured to correct the reference output specification by using the output specification correction degree to calculate the outputs of the display unit, the sound output unit, and the sensory stimulus output unit.

An information providing method according to an embodiment is for providing information to a user. The information providing method includes: detecting, as environment information surrounding an information providing device, position information of the information providing device; detecting, as biological information of the user, cerebral activation degree of the user; selecting, based on the environment information, one of a display unit configured to output a visual stimulus, a sound output unit configured to output an auditory stimulus, and a sensory stimulus output unit configured to output a sensory stimulus other than the visual stimulus and the auditory stimulus; deciding on a reference output specification for adjusting outputs of the display unit, the sound output unit, and the sensory stimulus output unit, based on the position information of the information providing device; and calculating an output specification correction degree for correcting the reference output specification, based on the cerebral activation degree of the user. The deciding of the reference output specification includes correcting the reference output specification by using the output specification correction degree to calculate the outputs of the display unit, the sound output unit, and the sensory stimulus output unit.

A non-transitory computer-readable storage medium according to an embodiment stores a computer program for providing information to a user. The computer program causes a computer to execute: detecting, as environment information surrounding an information providing device, position information of the information providing device; detecting, as biological information of the user, cerebral activation degree of the user; selecting, based on the environment information, one of a display unit configured to output a visual stimulus, a sound output unit configured to output an auditory stimulus, and a sensory stimulus output unit configured to output a sensory stimulus other than the visual stimulus and the auditory stimulus; deciding on a reference output specification for adjusting outputs of the display unit, the sound output unit, and the sensory stimulus output unit, based on the position information of the information providing device; and calculating an output specification correction degree for correcting the reference output specification, based on the cerebral activation degree of the user. The deciding of the reference output specification includes correcting the reference output specification by using the output specification correction degree to calculate the outputs of the display unit, the sound output unit, and the sensory stimulus output unit.

BRIEF DESCRIPTION OF THE DRAWINGS

FIG. 5 is a table for explaining an example of environment scores;

FIG. 6 is a table illustrating an example of environment patterns;

FIG. 8 is a table indicating the relationship of environment patterns with target devices and reference output specifications;

FIG. 10 is a table illustrating an example of the relationship between user states and output specification correction degrees; and FIG. 11 is a table illustrating an example of output restriction necessity information.

DETAILED DESCRIPTION

An exemplary embodiment is described below in detail with reference to the accompanying drawings. However, the present disclosure is not limited by the embodiment described below.

Information Providing Device

Figure 1:
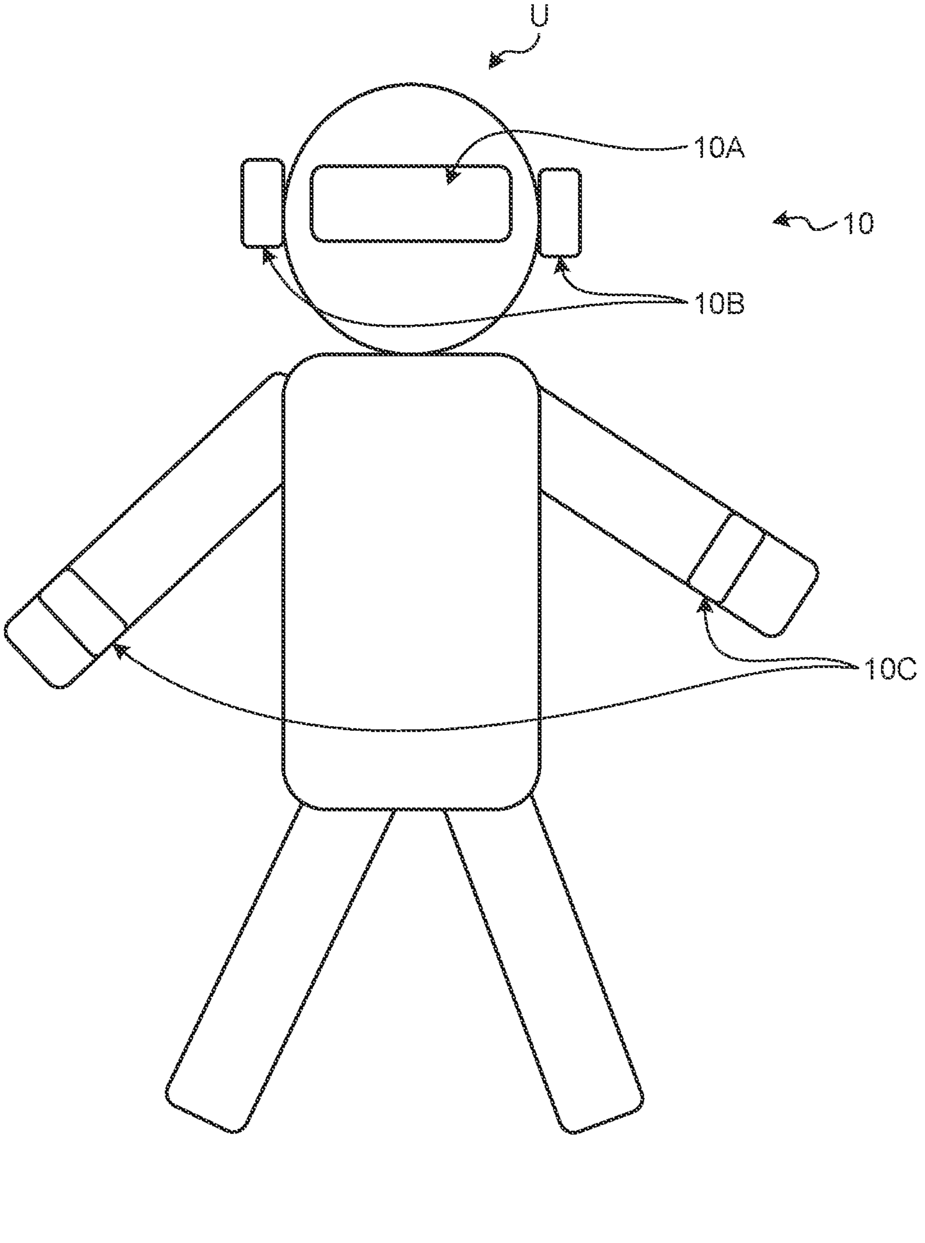
FIG. 1 is a schematic diagram of an information providing device according to an embodiment.

FIG. 1 is a schematic diagram of an information providing device according to the present embodiment. An information providing device 10 according to the present embodiment provides information to a user U by outputting visual stimuli, auditory stimuli, and sensory stimuli to the user U. A sensory stimulus represents a stimulus given to the senses other than the visual sense and the auditory sense. In the present embodiment, a tactile stimulus represents the sensory stimulus. However, a sensory stimulus is not limited to be a tactile stimulus, and can be a stimulus to any arbitrary sense other than the visual sense or the auditory sense. For example, a gustatory stimulus can be treated as a sensory stimulus, or an olfactory stimulus can be treated as a sensory stimulus, or two or more types of stimuli from among a tactile stimulus, a gustatory stimulus, and an auditory stimulus can be treated as a sensory stimulus. As illustrated in FIG. 1, the information providing device 10 is, what is called, a wearable device that is attached to the body of the user U. In the example given in the present embodiment, the information providing device 10 includes a device 10A that is attached to the eyes of the user U, devices 10B that are attached to the ears of the user U, and devices 10C that are attached to the arms of the user. The device 10A that is attached to the eyes of the user U includes a display unit 26A (explained later) for outputting visual stimuli (for displaying images) to the user. Each device 10B that is attached to an ear of the user U includes a sound output unit 26B (explained later) for outputting auditory stimuli (sounds) to the user U. Each device 10C that is attached to an arm of the user U includes a sensory stimulus output unit 26C (explained later) for outputting sensory stimuli to the user U. However, the configuration illustrated in FIG. 1 is only exemplary, and the number of devices as well as the attachment positions on the user U can be set in an arbitrary manner. Moreover, for example, the information providing device 10 is not limited to be a wearable device. Alternatively, the information providing device 10 can be a device carried along by the user U. For example, the information providing device 10 can be, what is called, a smartphone or a tablet terminal.

Environmental Image

Figure 2:
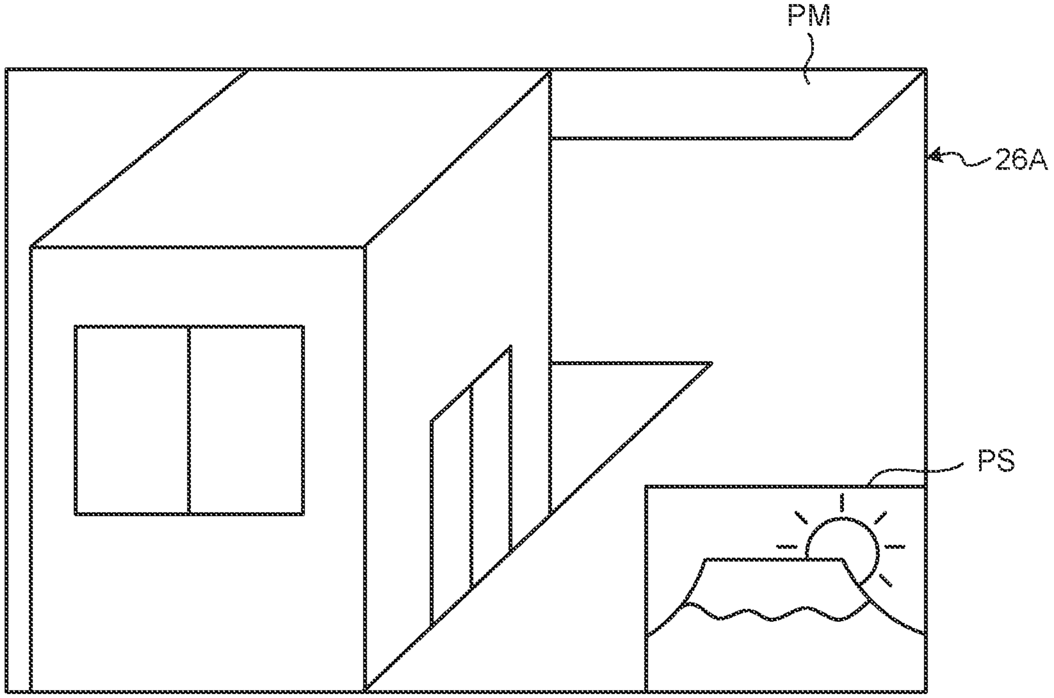
FIG. 2 is a diagram illustrating an exemplary image displayed in the information providing device.

FIG. 2 is a diagram illustrating an exemplary image displayed by the information providing device. As illustrated in FIG. 2, the information providing device 10 provides an environmental image PM to the user U via the display unit 26A. With that, the user U who is wearing the information providing device 10 becomes able to view the environmental image PM. In the present embodiment, the environmental image PM is the image of the scenery that would be visible to the user U without wearing the information providing device 10. Thus, the environmental image PM can also be said to be the image of the actual objects present within the field of view of the user U. In the present embodiment, the information providing device 10 provides the environmental image PM to the user U by, for example, letting the outside light (the ambient visible light) pass through the display unit 26A. That is, in the present embodiment, it can be said that the user U directly views the image of the actual scenery through the display unit 26A. However, the information providing device 10 is not limited to enable the user U to directly view the image of the actual scenery. Alternatively, an image of the environmental image PM can be displayed on the display unit 26A and provided to the user U via the display unit 26A. In that case, the user U views, as the environmental image PM, the image of the scenery as displayed on the display unit 26A. In that case, the information providing device 10 displays, as the environmental image PM on the display unit 26A, an image that is taken by a camera 20A (explained later) and that covers the field of view of the user U. With reference to FIG. 2, roads and a building are captured in the environmental image PM. However, that is merely an example.

Content Image

As illustrated in FIG. 2, the information providing device 10 displays a content image PS in the display unit 26A. The content image PS is an image of the objects other than the actual scenery present within the field of view of the user U. As long as the content image PS is an image including the information to be notified the user U, it can have any arbitrary type of content. For example, the content image PS can be a distribution image such as a movie or a television program, or can be a navigation image meant for showing the direction to the user U, or can be a notification image for notifying the user U about the reception of communication such as a phone call or an email, or can be an image including all of the above types of content. Moreover, the content image PS can be an image in which advertisements about products or services are not included.

In the example illustrated in FIG. 2, the content image PS is displayed on the display unit 26A and in a superimposed manner on the environmental image PM that is provided through the display unit 26A. Hence, the user U happens to view an image in which the content image PS is superimposed on the environmental image PM. However, the manner of displaying the content image PS is not limited to the superimposed pattern as illustrated in FIG. 2. The manner of displaying the content image PS, that is, the output specification (explained later) is set according to, for example, environment information. Regarding the environment information, the detailed explanation is given later.

Configuration of Information Providing Device

Figure 3:
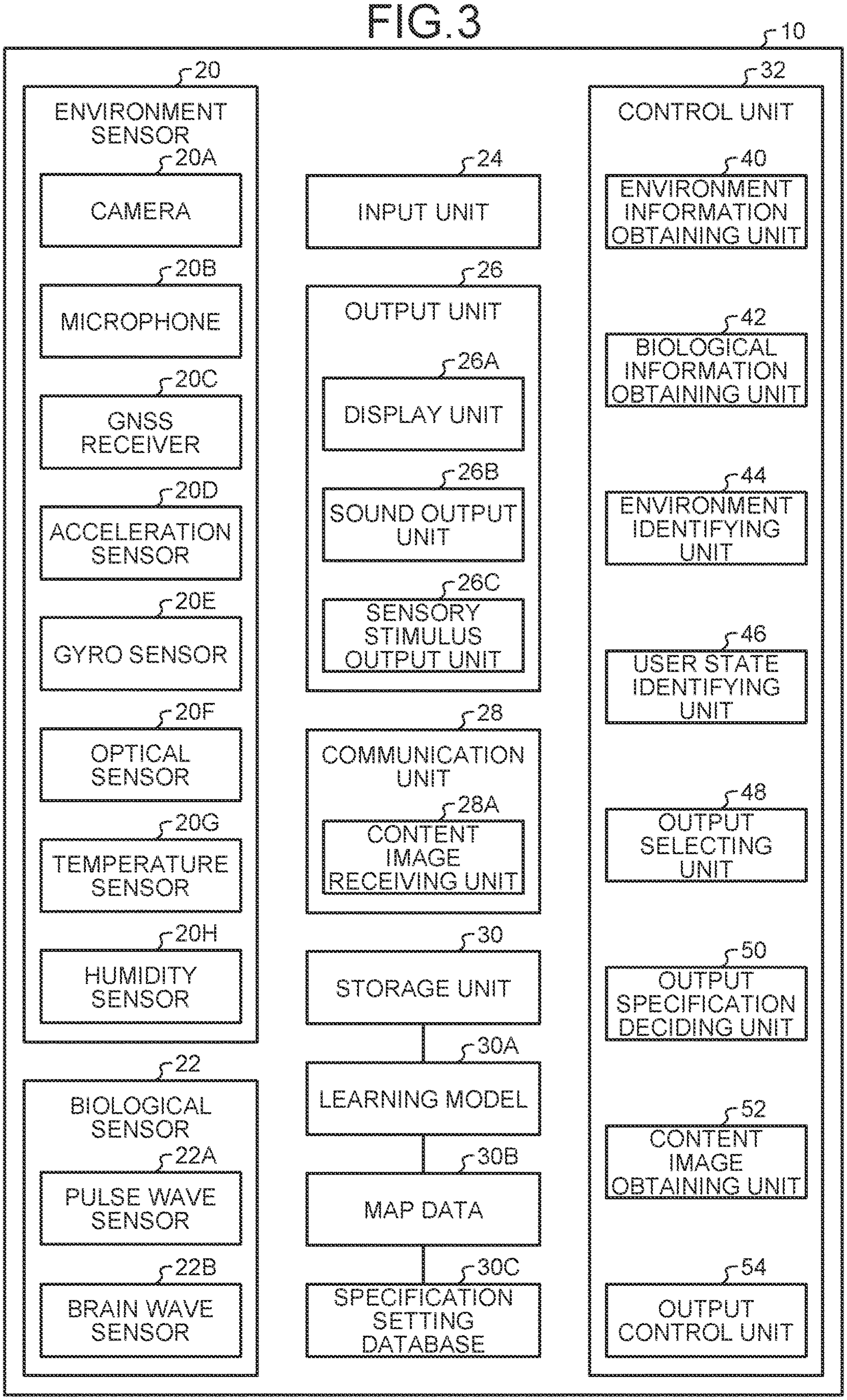
FIG. 3 is a schematic block diagram of the information providing device according to the present embodiment.

FIG. 3 is a schematic block diagram of the information providing device according to the present embodiment. As illustrated in FIG. 3, the information providing device 10 includes an environment sensor 20, a biological sensor 22, an input unit 24, an output unit 26, a communication unit 28, a storage unit 30, and a control unit 32.

Environment Sensor

The environment sensor 20 detects environment information of the surrounding of the information providing device 10. The environment information of the surrounding of the information providing device 10 can be said to be the information indicating the type of environment in which the information providing device 10 is present. Moreover, since the information providing device 10 is attached to the user U, the environment sensor 20 can also be said to detect the environment information of the surrounding of the user U.

The environment sensor 20 includes a camera 20A, a microphone 20B, a GNSS receiver 20C, an acceleration sensor 20D, a gyro sensor 20E, an light sensor 20F, a temperature sensor 20G, and a humidity sensor 20H. However, the environment sensor 20 can be an arbitrary sensor that detects the environment information; and, for example, either can include either one of the camera 20A, the microphone 20B, the GNSS receiver 20C, the acceleration sensor 20D, the gyro sensor 20E, the light sensor 20F, the temperature sensor 20G, and the humidity sensor 20H, or can include some other sensor.

The camera 20A is an imaging device that detects, as the environment information, the visible light of the surrounding of the information providing device 10 (the user U), and performs imaging of the surrounding of the information providing device 10 (the user U). The camera 20A can be a video camera that performs imaging at a predetermined framerate. In the information providing device 10, the position of installation and the orientation of the camera 20A can be set in an arbitrary manner. For example, the camera 20A can be installed in the device 10A illustrated in FIG. 1, and can be oriented to have the imaging direction toward the face of the user U. With that, the camera 20A becomes able to perform imaging of the objects present in the line of sight of the user U, that is, to perform imaging of the objects present within the field of vision of the user U. Meanwhile, it is possible to have an arbitrary number of cameras 20A. Thus, there can be only one camera 20A, or there can be a plurality of cameras 20A. When a plurality of cameras 20A is used, the information about the orientation directions of the cameras 20A is also obtained.

The microphone 20B detects, as the environment information, the sounds (sound wave information) generated in the surrounding of the information providing device 10 (the user U). In the information providing device 10, the position of installation, the orientation, and the count of the microphone 20B can be set in an arbitrary manner. When a plurality of microphones 20B is used, the information about the orientation directions of the microphones 20B is also obtained.

The GNSS receiver 20C detects, as the environment information, the position information of the information providing device 10 (the user U). Herein, the position information represents the global coordinates. In the present embodiment, the GNSS receiver 20C is, what is called, a GNSS module (GNSS stands for a Global Navigation Satellite System) that receives radio waves from satellites and outputs the position information of the information providing device 10 (the user U).

The acceleration sensor 20D detects, as the environment information, the acceleration of the information providing device 10 (the user U). For example, the acceleration sensor 20D detects the gravitational force, vibrations, and impact shocks.

The gyro sensor 20E detects, as the environment information, the rotation and the orientation of the information providing device 10 (the user U) using the principle of the Coriolis force, or the Euler force, or the centrifugal force.

The light sensor 20F detects, as the environment information, the intensity of the light in the surrounding of the information providing device 10 (the user U). The light sensor 20F is capable of detecting the intensity of the visible light, the infrared light, or the ultraviolet light.

The temperature sensor 20G detects, as the environment information, the surrounding temperature of the information providing device 10 (the user U).

The humidity sensor 20H detects, as the environment information, the surrounding humidity of the information providing device 10 (the user U).

Biological Sensor

The biological sensor 22 detects the biological information of the user U. As long as the biological information of the user U can be detected, the biological sensor 22 can be installed at an arbitrary position. It is desirable that the biological information is not unalterable information such as fingerprint information, but is information that, for example, undergoes changes in its value according to the condition of the user U. More specifically, it is desirable that the biological information represents the information related to the autonomic nerves of the user U, that is, represents the information that undergoes changes regardless of the will of the user U. More particularly, the biological sensor 22 includes a pulse wave sensor 22A and a brain wave sensor 22B, and detects the pulse waves and the brain waves of the user U as the biological information.

The pulse wave sensor 22A detects the pulse waves of the user U. For example, the pulse wave sensor 22A can be a transmission-type photoelectric sensor that includes a light emitting unit and a light receiving unit. In that case, the pulse wave sensor 22A is configured in such a way that, for example, the light emitting unit and the light receiving unit face each other across a fingertip of the user U; and the light that has passed through the fingertip is received in the light receiving unit and the pulse waveform is measured using the fact that the blood flow increases in proportion to the pressure of the pulse waves. However, the pulse wave sensor 22A is not limited to have the configuration explained above, and can be configured in an arbitrary manner as long as the pulse waves can be detected.

The brain wave sensor 22B detects the brain waves of the user U. As long as the brain waves can be detected, the brain wave sensor 22B can have an arbitrary configuration. For example, in principle, as long as an understanding is gained regarding the waves, such as the α waves and the β waves, and regarding the activity of the basic pattern (the background brain waves) appearing in the entire brain and as long as the enhancement or the decline in the activity of the entire brain can be detected; it is sufficient if a few brain wave sensors 22B can be installed. In the present embodiment, unlike the electroencephalography done for medical purpose, it serves the purpose as long as the approximate changes in the condition of the user U can be measured. Hence, for example, the configuration can be such that only two electrodes are attached to the forehead and the ears, and extremely simplistic surface brain waves are detected.

Meanwhile, the biological sensor 22 is not limited to only detect the pulse waves and the brain waves as the biological information. Alternatively, for example, the biological sensor 22 can detect at least either the pulse waves or the brain waves. Still alternatively, the biological sensor 22 can detect some other factors other than the pulse waves and the brain waves as the biological information. For example, the biological sensor 22 can detect the amount of perspiration or the pupil size. Meanwhile, the biological sensor 22 is not a part of the mandatory configuration, and need not be installed in the information providing device 10.

Input Unit

The input unit 24 receives user operations and, for example, can be a touch-sensitive panel.

Output Unit

The output unit 26 outputs stimuli for at least one of the five senses of the user U. More particularly, the output unit 26 includes the display unit 26A, the sound output unit 26B, and a sensory stimulus output unit 26C. The display unit 26A displays images and outputs sensory stimuli to the user U. In other words, the display unit 26A can be said to be a visual stimulus output unit. In the present embodiment, the display unit 26A is, what is called, a head-mounted display (HMD). As explained above, the display unit 26A displays the content image PS. The sound output unit 26B is a device (speaker) that outputs sounds for the purpose of outputting auditory stimuli to the user U. In other words, the sound output unit 26B can be said to be an auditory stimulus output unit. The sensory stimulus output unit 26C outputs sensory stimuli to the user U. In the present embodiment, the sensory stimulus output unit 26C outputs tactile stimuli. For example, the sensory stimulus output unit 26C is a vibration motor such as a vibrator that operates according to a physical factor such as vibrations and outputs tactile stimuli. However, the type of tactile stimulation is not limited to vibrations, and some other type can also be used.

In this way, the output unit 26 stimulates, from among the five senses of a person, the visual sense, the auditory sense, and one of the other senses other than the visual sense and the auditory sense (i.e., in the present embodiment, the tactile sense). However, the output unit 26 is not limited to output visual stimuli, auditory stimuli, one of the other stimuli other than visual stimuli and auditory stimuli. For example, the output unit 26 can output at least one type of stimuli from among visual stimuli, auditory stimuli, and one of the other stimuli other than visual stimuli and auditory stimuli; or can output at least visual stimuli (by displaying images); or can output either auditory stimuli or tactile stimuli in addition to outputting visual stimuli; or can output at least either visual stimuli, auditory stimuli, and tactile stimuli along with outputting at least one of the remaining types of sensory stimuli (that is, at least either gustatory stimuli or olfactory stimuli).

Communication Unit

The communication unit 28 is a module for communicating with external devices and, for example, can include an antenna. In the present embodiment, wireless communication is implemented as the communication method in the communication unit 28. However, any arbitrary communication method can be implemented. The communication unit 28 includes a content image receiving unit 28A that functions as a receiver for receiving content image data which represents the image data of content images. Sometimes the content displayed in a content image includes a sound or includes a sensory stimulus other than a visual stimulus and an auditory stimulus. In that case, as the content image data, the content image receiving unit 28A can receive the image data of a content image as well as receive sound data and sensory stimulus data. Thus, the data of a content image is received by the content image receiving unit 28A as explained above. Alternatively, for example, the data of content images can be stored in advance in the storage unit 30, and the content image receiving unit 28A can receive the data of a content image from the storage unit 30.

Storage Unit

The storage unit 30 is a memory used to store a variety of information such as the arithmetic operation details of the control unit 32 and computer programs. For example, the storage unit 30 includes at least either a main memory device, such as a random access memory (RAM) or a read only memory (ROM), or an external memory device such as a hard disk drive (HDD).

The storage unit 30 is used to store a learning model 30A, map data 30B, and a specification setting database 30C. The learning model 30A is an AI model used for identifying, based on the environment information, the environment around the user U. The map data 30B contains the position information of actual building structures and natural objects, and can be said to be the data in which the global coordinates are associated to actual building structures and natural objects. The specification setting database 30C is used to store the information meant for deciding on the display specification of the content image PS as explained later. Regarding the operations performed using the learning model 30A, the map data 30B, and the specification setting database 30C, the explanation is given later. Meanwhile, the learning model 30A, the map data 30B, and the specification setting database 30C as well as the computer programs to be executed by the control unit 32 and stored in the storage unit 30 can be alternatively stored in a recording medium that is readable by the information providing device 10. Meanwhile, neither the computer programs to be executed by the control unit 32 and stored in the storage unit 30 nor the learning model 30A, the map data 30B, and the specification setting database 30C are limited to be stored in advance in the storage unit 30. Alternatively, at the time of using any data, the information providing device 10 can obtain that data from an external device by performing communication.

Control Unit

The control unit 32 is an arithmetic device, that is, a central processing unit (CPU). The control unit 32 includes an environment information obtaining unit 40, a biological information obtaining unit 42, an environment identifying unit 44, a user state identifying unit 46, an output selecting unit 48, an output specification deciding unit 50, a content image obtaining unit 52, and an output control unit 54. The control unit 32 reads a computer program (software) from the storage unit 30 and executes it so as to implement the operations of the environment information obtaining unit 40, the biological information obtaining unit 42, the environment identifying unit 44, the user state identifying unit 46, the output selecting unit 48, the output specification deciding unit 50, the content image obtaining unit 52, and the output control unit 54. Meanwhile, the control unit 32 can perform such operations either using a single CPU or using a plurality of CPUs when installed therein. Moreover, at least some units from among the environment information obtaining unit 40, the biological information obtaining unit 42, the environment identifying unit 44, the user state identifying unit 46, the output selecting unit 48, the output specification deciding unit 50, the content image obtaining unit 52, and the output control unit 54 can be implemented using hardware.

The environment information obtaining unit 40 controls the environment sensor 20 and causes it to detect the environment information. Thus, the environment information obtaining unit 40 obtains the environment information detected by the environment sensor 20. Regarding the operations performed by the environment information obtaining unit 40, the explanation is given later. Meanwhile, if the environment information obtaining unit 40 is implemented using hardware, then it can also be called an environment information detector.

The biological information obtaining unit 42 controls the biological sensor 22 and causes it to detect the biological information. Thus, the biological information obtaining unit 42 obtains the environment information detected by the biological sensor 22. Regarding the operations performed by the biological information obtaining unit 42, the explanation is given later. Meanwhile, if the biological information obtaining unit 42 is implemented using hardware, then it can also be called a biological information detector. Moreover, the biological information obtaining unit 42 is not a mandatory part of the configuration.

The environment identifying unit 44 identifies, based on the environment information obtained by the environment information obtaining unit 40, the environment around the user U. Then, the environment identifying unit 44 calculates an environment score representing the score for identifying the environment; and, based on the environment score, identifies an environment condition pattern indicating the condition of the environment and accordingly identifies the environment. Regarding the environment identifying unit 44, the explanation is given later.

The user state identifying unit 46 identifies the condition of the user U based on the biological information obtained by the biological information obtaining unit 42. Regarding the operations performed by the user state identifying unit 46, the explanation is given later. Meanwhile, the user state identifying unit 46 is not a mandatory part of the configuration.

The output selecting unit 48 selects, based on at least either the environment information obtained by the environment information obtaining unit 40 or the biological information obtained by the biological information obtaining unit 42, the target device to be operated from among the devices in the output unit 26. Regarding the operations performed by the output selecting unit 48, the explanation is given later. Meanwhile, if the output selecting unit 48 is implemented using hardware, then it can also be called a sense selector. In the case in which the output specification deciding unit 50 (explained later) decides on the output specification based on the environment information, the output selecting unit 48 need not be used. In that case, for example, instead of selecting the target device, the information providing device 10 can operate all constituent elements of the output unit 26, that is, can operate the display unit 26A, the sound output unit 26B, and the sensory stimulus output unit 26C.

The output specification deciding unit 50 decides on the output specification of a stimulus (herein, a visual stimulus, an auditory stimulus, or a tactile stimulus), which is to be output by the output unit 26, based on at least either the environment information obtained by the environment information obtaining unit 40 or the biological information obtained by the biological information obtaining unit 42. For example, it can be said that, based on at least either the environment information obtained by the environment information obtaining unit 40 or the biological information obtained by the biological information obtaining unit 42, the output specification deciding unit 50 decides on the display specification (the output specification) of the content image PS displayed on the display unit 26A. The output specification represents the index about the manner of outputting the stimulus that is output by the output unit 26. Regarding the output specification, the detailed explanation is given later. Moreover, regarding the operations performed by the output specification deciding unit 50, the explanation is given later. Meanwhile, in the case in which the output selecting unit 48 selects the target device based on the environment information, the output specification deciding unit 50 need not be included. In that case, for example, in the information providing device 10, without deciding on the output specification according to the environment information, the selected target device can be made to output a stimulus according to an arbitrary output specification.

The content image obtaining unit 52 obtains the content image data via the content image receiving unit 28A.

The output control unit 54 controls the output unit 26 and causes it to perform output. The output control unit 54 ensures that the target device selected by the output selecting unit 48 performs output according to the output specification decided by the output specification deciding unit 50. For example, the output control unit 54 displays the content image PS, which is obtained by the content image obtaining unit 52, in a superimposed manner on the main image PM and according to the display specification decided by the output specification deciding unit 50. Meanwhile, if the output control unit 54 is implemented using hardware, then it can also be called a multisensory provider.

Thus, the information providing device 10 is configured in the manner explained above.

Operation Details

Figure 4:
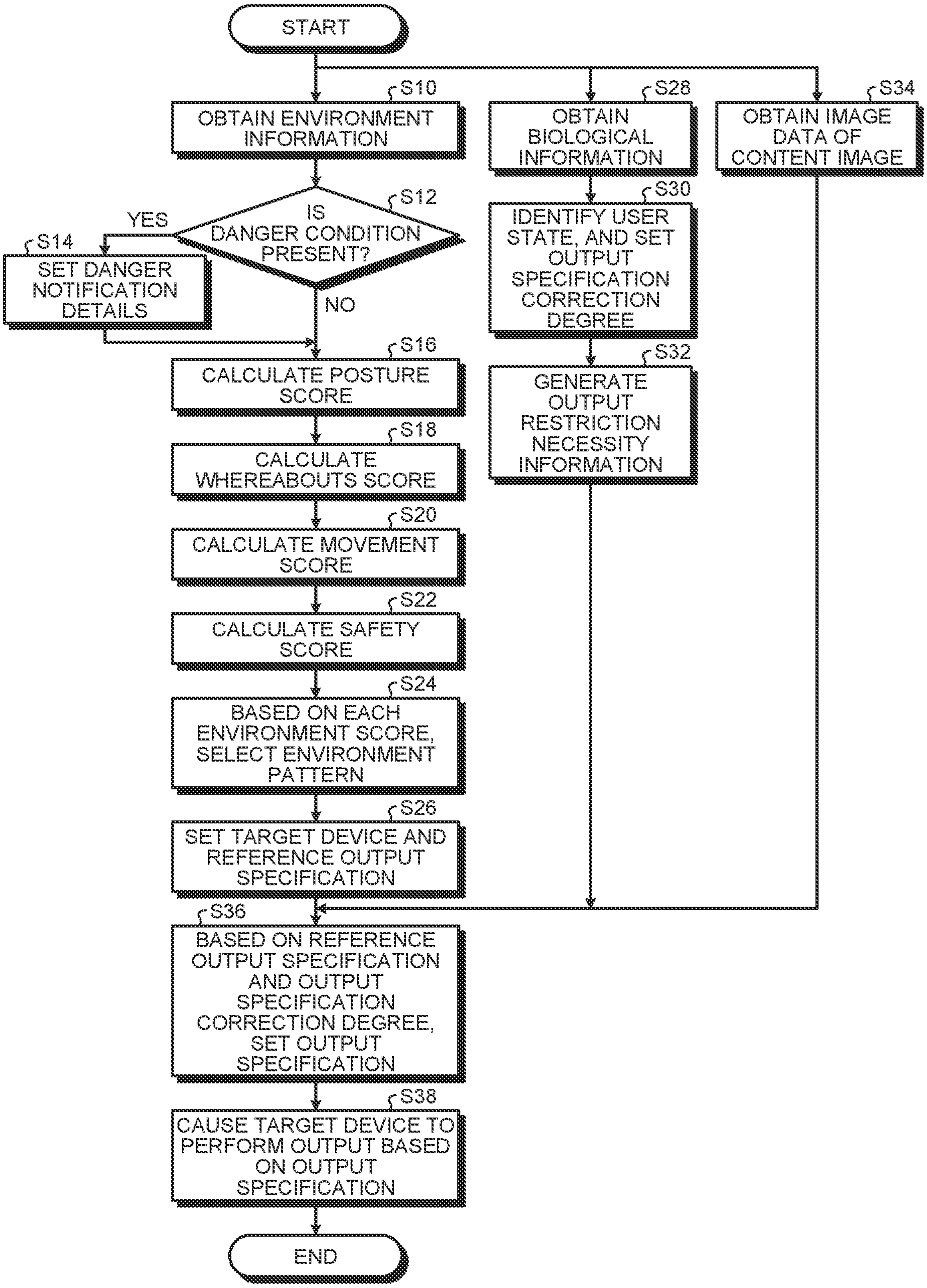
FIG. 4 is a flowchart for explaining the operation details of the information providing device according to the present embodiment.

Given below is the explanation of the operation details of the information providing device 10. More specifically, given below is the explanation of the operation details that the output unit 26 is made to output based on the environment information or the biological information. FIG. 4 is a flowchart for explaining the operation details of the information providing device according to the present embodiment.

Acquisition of Environment Information

As illustrated in FIG. 4, in the information providing device 10, the environment information obtaining unit 40 obtains the environment information detected by the environment sensor 20 (Step S10). In the present embodiment, the environment information obtaining unit 40 obtains, from the camera 20A, the image data in which the surrounding of the information providing device 10 (the user U) is captured; obtains, from the microphone 20B, the sound data of the surrounding of the information providing device 10 (the user U); obtains, from the GNSS receiver 20C, the position information of the information providing device 10 (the user U); obtains, from the acceleration sensor 20D, the acceleration information of the information providing device 10 (the user U); obtains, from the gyro sensor 20E, the orientation information, that is, the posture information of the information providing device 10 (the user U); obtains, from the light sensor 20F, the intensity information about the infrared light or the ultraviolet light of the surrounding of the information providing device 10 (the user U); obtains, from the temperature sensor 20G, the temperature information of the surrounding of the information providing device 10 (the user U); and obtains, from the humidity sensor 20H, the humidity information of the surrounding of the information providing device 10 (the user U). The environment information obtaining unit 40 sequentially obtains such environment information at regular intervals. The environment information obtaining unit 40 can obtain the sets of environment information either at the same timing or at mutually different timings. Moreover, the regular intervals for obtaining the sets of environment information can be set in an arbitrary manner. Thus, the regular interval can be set to be either same or different for each set of environment information.

Determining Danger Condition

In the information providing device 10, after the environment information is obtained, based on that environment information, the environment identifying unit 44 determines whether a danger condition is present indicating that the surrounding environment around the user U is dangerous (Step S12).

The environment identifying unit 44 determines whether a danger condition is present based on an image of the surrounding of the information providing device 10 as taken by the camera 20A. In the following explanation, an image of the surrounding of the information providing device 10 as taken by the camera 20A is referred to as a surrounding image. For example, the environment identifying unit 44 identifies the object captured in the surrounding image and, based on the type of the identified object, determines whether a danger condition is present. More specifically, if the object captured in the surrounding image is a specific object set in advance, then the environment identifying unit 44 determines that a danger condition is present. However, if the object is not a specific object, then the environment identifying unit 44 determines that a danger condition is not present. Herein, the specific objects can be set in an arbitrary manner. For example, a specific object can be an object that is likely to create a danger to the user U, such as the flames indicating that a fire has broken, a vehicle, or a signboard indicating that some work is going on. Meanwhile, the environment identifying unit 44 can determine whether a danger condition is present based on a plurality of surrounding images successively taken in chronological order. For example, in each of a plurality of surrounding images successively taken in chronological order, the environment identifying unit 44 identifies an object and determines whether that object is a specific object and is the same object. If the same specific object is captured, then the environment identifying unit 44 determines whether the specific object captured in the subsequent surrounding images, which are captured later in the chronological order, has grown relatively larger, that is, determines whether the specific object has been moving closer to the user U. If the specific object captured in the subsequent surrounding images, which are captured later in the chronological order, has grown relatively larger, that is, if the specific object has been moving closer to the user U; then the environment identifying unit 44 determines that a danger condition is present. On the other hand, if the specific object captured in the subsequent surrounding images, which are captured later in the chronological order, has not grown relatively larger, that is, if the specific object has not been moving closer to the user U; then the environment identifying unit 44 determines that a danger condition is not present. In this way, the environment identifying unit 44 can determine about a danger condition either based on a single surrounding image or based on a plurality of surrounding images successively taken in chronological order. For example, the environment identifying unit 44 can switch between the determination method depending on the type of object captured in the surrounding images. Thus, if a specific object such as flames indicating a fire is captured that can be determined to be dangerous from a single surrounding image, then the environment identifying unit 44 can determine that a danger condition is present based on the single surrounding image. Alternatively, for example, if a specific object such as a vehicle is captured that cannot be determined to be dangerous, then the environment identifying unit 44 can determine about the danger condition based on a plurality of images successively taken in chronological order.

Meanwhile, the environment identifying unit 44 can identify an object, which is captured in a surrounding image, according to an arbitrary method. For example, the environment identifying unit 44 can identify the object using the learning model 30A. In that case, for example, the learning model 30A is an AI model in which the data of an image and the information indicating the type of the object captured in that image is treated as a single dataset and which is built by performing learning using a plurality of such datasets as the teacher data. The environment identifying unit 44 inputs the image data of a surrounding image to the already-learnt learning model 30A, obtains the information about the identification of the type of the object captured in that surrounding image, and identifies the object.

Meanwhile, in addition to referring to a surrounding image, the environment identifying unit 44 can also refer to the position information obtained by the GNSS receiver 20C and then determine whether a danger condition is present. In that case, based on the position information of the information providing device 10 (the user U) as obtained by the GNSS receiver 20C and based on the map data 30B, the environment identifying unit 44 obtains location information indicating the location of the user U. The location information indicates the type of the place at which the user U (the information providing device 10) is present. That is, for example, the location information indicates that the user U is at a shopping center or on a road. The environment identifying unit 44 reads the map data 30B, identifies the types of building structures or the types of natural objects present within a predetermined distance from the current position of the user U, and identifies the location information from the building structures or the natural objects. For example, if the current position of the user U overlaps with the coordinates of a shopping center, then the fact that the user U is present in a shopping center is identified as the location information. Subsequently, if the location information has a specific relationship with the type of object identified from the surrounding image, then the environment identifying unit 44 determines that a danger condition is present. On the other hand, if the specific relationship is not established, then the environment identifying unit 44 determines that a danger condition is not present. The specific relationship can be set in an arbitrary manner. For example, such a combination of an object and a place which is likely to create a danger when that object is present at that place can be set as the specific relationship.

Moreover, the environment identifying unit 44 determines whether a danger condition is present based on the sound information obtained by the microphone 20B. In the following explanation, the sound information of the surrounding of the information providing device 10 as obtained by the microphone 20B is referred to as a surrounding sound. For example, the environment identifying unit 44 identifies the type of the sound included in the surrounding sound and, based on the identified type of the sound, determines whether a danger condition is present. More specifically, if the type of the sound included in the surrounding sound is a specific sound that is set in advance, then the environment identifying unit 44 can determine that a danger condition is present. On the other hand, if no specific sound is included, then the environment identifying unit 44 can determine that a danger condition is not present. The specific sound can be set in an arbitrary manner. For example, a specific sound can be a sound that is likely to create a danger to the user U, such as a sound indicating that a fire has broken, the sound of a vehicle, or a sound indicating that some work is going on.

Meanwhile, the environment identifying unit 44 can identify the type of the sound included in the surrounding sound according to an arbitrary method. For example, the environment identifying unit 44 can identify the object using the learning model 30A. In that case, for example, the learning model 30A is an AI model in which sound data (for example, data indicating the frequency and the intensity of a sound) and the information indicating the type of that sound is treated as a single dataset and which is built by performing learning using a plurality of such datasets as the teacher data.

The environment identifying unit 44 inputs the sound data of a surrounding sound to the already-learnt learning model 30A, obtains the information about the identification of the type of the sound included in that surrounding sound, and identifies the type of the sound.

Meanwhile, in addition to referring to the surrounding sound, the environment identifying unit 44 can also refer to the position information obtained by the GNSS receiver 20C and then determine whether a danger condition is present. In that case, based on the position information of the information providing device 10 (the user U) as obtained by the GNSS receiver 20C and based on the map data 30B, the environment identifying unit 44 obtains location information indicating the location of the user U. Subsequently, if the location information has a specific relationship with the type of the sound identified from the surrounding sound, then the environment identifying unit 44 determines that a danger condition is present. On the other hand, if the specific relationship is not established, then the environment identifying unit 44 determines that a danger condition is not present. The specific relationship can be set in an arbitrary manner. For example, such a combination of a sound and a place that is likely to create a danger when that sound is generated at that place can be set as the specific relationship.

In this way, in the present embodiment, the environment identifying unit 44 determines about a danger condition based on the surrounding image and the surrounding sound. However, the determination method about the danger condition is not limited to the method explained above, and any arbitrary method can be implemented. For example, the environment identifying unit 44 can determine about the danger condition based on either the surrounding image or the surrounding sound. Alternatively, the environment identifying unit 44 can determine about the danger condition based on at least either the image of the surrounding of the information providing device 10 as taken by the camera 20A, or the sound of the surrounding of the information providing device 10 as detected by the microphone 20B, or the position information obtained by the GNSS receiver 20C. Meanwhile, in the present embodiment, the determination of a danger condition is not mandatory and can be omitted.

Setting of Danger Notification Details

If it is determined that a danger condition is present (Yes at Step S10); then, in the information providing device 10, the output control unit 54 sets danger notification details that represent the notification details about the existence of a danger condition (Step S12). Based on the details of the danger condition, the information providing device 10 sets the danger notification details. The details of the danger condition represent the information indicating the type of the danger, and are identified from the type of the object captured in the surrounding image or from the type of the sound included in the surrounding sound. For example, if the object is a car that is approaching, then the details of the danger condition indicate that "a vehicle is approaching." The danger notification details represent the information indicating the details of the danger condition. For example, if the details of the danger condition indicate that a vehicle is approaching, then the danger notification contents represent the information indicating that a vehicle is approaching.

The danger notification details differ according to the type of the target device selected at Step S26 (explained later). For example, if the display unit 26A is selected as the target device, then the danger notification details indicate the display details (content) of the content image PS. That is, the danger notification details are displayed in the form of the content image PS. In that case, for example, the danger notification details represent image data indicating the details such as "Beware! A vehicle is approaching." Alternatively, if the sound output unit 26B is selected as the target device, then the danger notification details represent the details of the sound output from the sound output unit 26B. In this case, for example, the danger notification details represent sound data for making a sound such as "please be careful as a vehicle is approaching." Still alternatively, if the sensory stimulus output unit 26C is selected as the target device, then the danger notification details represent the details of the sensory stimulus output from the sensory stimulus output unit 26C. In this case, for example, the danger notification details indicate a tactile stimulus meant for gaining attention of the user U.

Meanwhile, the operation of setting the danger notification details at Step S14 can be performed at an arbitrary timing after it is determined at Step S12 that a danger condition is present and before the operation of outputting the danger notification details at Step S38 performed later. For example, the operation of setting the danger notification details at Step S14 can be performed after the selection of the target device at Step S32 performed later.

Calculation of Environment Score

If it is determined that a danger condition is not present (No at Step S12); then, in the information providing device 10, the environment identifying unit 44 calculates various environment scores based on the environment information as indicated from Step S16 to Step S22. An environment score represents a score for identifying the environment in which the user U (the information providing device 10) is present. More particularly, the environment identifying unit 44 calculates the following scores as the environment scores: a posture score (Step S16), a location score (Step S18), a movement score (Step S20), and a safety score (Step S22). The sequence of operations performed between Steps S16 and S22 is not limited to the sequence given above, and an arbitrary sequence can be implemented. Meanwhile, also when the danger notification details are set at Step S14, various environment scores are calculated from Step S16 to Step S22. Given below is the specific explanation of the environment scores.

FIG. 5 is a table for explaining an example of the environment scores. As illustrated in FIG. 5, the environment identifying unit 44 calculates an environment score for each environment category. An environment category indicates a type of the environment around the user U. In the example illustrated in FIG. 5, the environment categories include the posture of the user U, the location of the user U, the movement of the user U, and the safety of the surrounding environment of the user U. Moreover, the environment identifying unit 44 divides each environment category into more specific subcategories and calculates an environment score for each sub-category.

Posture Score

The environment identifying unit 44 calculates posture scores as environment scores for the category indicating the posture of the user U. A posture score represents the information indicating a posture of the user U, and can be said to indicate a numerical value about a type of the posture of the user U. The environment identifying unit 44 calculates posture scores based on the environment information that, from among a plurality of types of environment information, is related to the postures of the user U. Examples of the environment information related to the postures of the user U include the surrounding image obtained by the camera 20A and the orientation of the information providing device 10 as detected by the gyro sensor 20E.

More specifically, in the example illustrated in FIG. 5, the category indicating the posture of the user U includes a sub-category indicating the standing state and a sub-category indicating that the face orientation is in the horizontal direction. Based on the surrounding image obtained by the camera 20A, the environment identifying unit 44 calculates a posture score for the sub-category indicating the standing state. The posture score for the sub-category indicating the standing state can be said to be a numerical value indicating the degree of coincidence of the posture of the user U with respect to the standing state. Herein, an arbitrary method can be implemented for calculating the posture score for the sub-category indicating the standing state. For example, the posture score can be calculated using the learning model 30A. In that case, for example, the learning model 30A is an AI model in which the image data of the scenery captured in the field of view of a person and the information indicating whether the person is standing is treated as a single dataset and which is built by performing learning using a plurality of such datasets as the teacher data. The environment identifying unit 44 inputs the image data of a surrounding image to the already-learnt learning model 30A, obtains the numerical value indicating the degree of coincidence with respect to the standing state, and treats the numerical value as the posture score. Herein, although the degree of coincidence with respect to the standing state is taken into account, the standing state is not the only possible state. Alternatively, for example, the degree of coincidence can be calculated with respect to the seated state or the sleeping state.

Moreover, based on the orientation of the information providing device 10 as detected by the gyro sensor 20E, the environment identifying unit 44 calculates the posture score for the sub-category indicating that the face orientation is in the horizontal direction. The posture score for the sub-category indicating that the face orientation is in the horizontal direction can be said to be the numerical value indicating the degree of coincidence of the posture (the orientation of the face) of the user U with respect to the horizontal direction. In order to calculate the posture score for the sub-category indicating that the face orientation is in the horizontal direction, any arbitrary method can be implemented. Herein, although the degree of coincidence with respect to the fact that the face orientation is in the horizontal direction is taken into account, the horizontal direction is not the only possible direction. Alternatively, for example, the degree of coincidence can be calculated with respect to the fact that the face is oriented in an arbitrary direction.

In this way, it can be said that the environment identifying unit 44 sets the information indicating the postures of the user U (herein, the posture scores) based on the surrounding image and the orientation of the information providing device 10. However, in order to set the information indicating the postures of the user U, the environment identifying unit 44 is not limited to use the surrounding image and the orientation of the information providing device 10, and alternatively can use arbitrary environment information. For example, the environment identifying unit 44 can use at least either the surrounding image or the orientation of the information providing device 10.

Location Scores

The environment identifying unit 44 calculates location scores as the environment scores regarding the location category of the user U. That is, a location score represents information indicating the location of the user U, and can be said to be the information indicating, in the form of a numerical value, the type of the place at which the user U is present. The environment identifying unit 44 calculates the location score based on the environment information that, from among a plurality of types of environment information, is related to the location of the user U. Examples of the environment information related to the location of the user U include the surrounding image obtained by the camera 20A, the position information of the information providing device 10 as obtained by the GNSS receiver 20C, and the surrounding sound obtained by the microphone 20B.

More specifically, in the example illustrated in FIG. 5, the category of the location of the user U includes a sub-category indicating the presence inside a train car, a sub-category indicating the presence on railway track, and a sub-category indicating the sound from the inside of a train car. Based on the surrounding image obtained by the camera 20A, the environment identifying unit 44 calculates the location score for the sub-category indicating the presence inside a train car. The location score for the sub-category indicating the presence inside a train car can be said to be a numerical value indicating the degree of coincidence of the user U with respect to a place such as inside a train car. In order to calculate the location score for the sub-category indicating the presence inside a train car, an arbitrary method can be implemented. For example, the location score can be calculated using the learning model 30A. In that case, for example, the learning model 30A is an AI model in which the image data of the scenery captured in the field of view of a person and the information indicating whether the person is present in a train car is treated as a single dataset and which is built by performing learning using a plurality of such datasets as the teacher data. The environment identifying unit 44 inputs the image data of a surrounding image to the already-learnt learning model 30A, obtains the numerical value indicating the degree of coincidence with respect to the location such as inside a train car, and treats the numerical value as the location score. Herein, although the degree of coincidence with respect to the location such as inside a train car is taken into account, that is not the only possible case. Alternatively, for example, the degree of coincidence can be calculated with respect to the fact that the person is present in an arbitrary type of vehicle.

Regarding the sub-category indicating the presence on railway track, the environment identifying unit 44 calculates the location score based on the position information of the information providing device 10 as obtained by the GNSS receiver 20C. The location score for the sub-category indicating the presence on railway track can be said to a numerical value indicating the degree of coincidence of the user U with respect to the place such as the railway track. In order to calculate the location score for the sub-category indicating the presence on railway track, an arbitrary method can be implemented. For example, the location score can be calculated using the map data 30B. For example, after reading the map data 30B, if the current position of the user U overlaps with the coordinates of the railway track, then the environment identifying unit 44 calculates the location score in such a way that the degree of coincidence of the place indicating the railway track with respect to the location of the user U becomes higher. Herein, although the degree of coincidence with respect to the railway track is taken into account, that is not the only possible case. Alternatively, the degree of coincidence with respect to a building structure or a natural object of an arbitrary type can be calculated.

Regarding the sub-category indicating the sound from the inside of a train car, the environment identifying unit 44 calculates the location score based on the surrounding sound obtained by the microphone 20B. The location score for the sub-category indicating the sound from the inside of a train car can be said to be a numerical value indicating the degree of coincidence of the surrounding sound with respect to the sound from the inside of a train car. Herein, in order to calculate the location score for the sub-category indicating the sound from the inside of a train car, an arbitrary method can be implemented. For example, the determination can be performed in an identical manner to the abovementioned method in which, based on the surrounding sound, it is determined whether a danger condition is present. That is, for example, the determination can be performed by determining whether the surrounding sound is a sound of a specific type. Meanwhile, although the degree of coincidence with respect to the sound from the inside of a train car is calculated, that is not the only possible case. Alternatively, the degree of coincidence with respect to the sound at an arbitrary place can be calculated.

In this way, it can be said that the environment identifying unit 44 sets the information indicating the location of the user U (herein, sets the location score) based on the surrounding image, based on the surrounding sound, and based on the position information of the information providing device 10. However, in order to set the information indicating the location of the user U, the environment identifying unit 44 is not limited to use the surrounding image, the surrounding sound, and the position information of the information providing device 10; and can alternatively use arbitrary environment information. For example, the environment identifying unit 44 can use at least either the surrounding image, or the surrounding sound, or the position information of the information providing device 10.

Movement Score

The environment identifying unit 44 calculates a movement score as the environment score for the category indicating the movement of the user U. Thus, the movement score can be said to be the information about a numerical value indicating the manner of movement of the user U. The environment identifying unit 44 calculates the movement score based on the environment information that, from among a plurality of types of environment information, is related to the movement of the user U. Examples of the environment information related to the movement of the user U include the acceleration information obtained by the acceleration sensor 20D.

More specifically, in the example illustrated in FIG. 5, the category indicating the movement of the user U includes a sub-category indicating the state of being in motion. The environment identifying unit 44 calculates, based on the acceleration information of the information providing device 10 as obtained by the acceleration sensor 20D, the location score for the sub-category indicating the state of being in motion. The movement score for the sub-category indicating the state of being in motion can be said to be a numerical value indicating the degree of coincidence of the present situation of the user U with respect to the fact that the user U is in motion. In order to calculate the movement score for the sub-category indicating the state of being in motion, an arbitrary method can be implemented. For example, the movement score can be calculated from the variation in the acceleration during a predetermined period of time. For example, when there is variation in the acceleration during a predetermined period of time, the movement score is calculated in such a way that the degree of coincidence with respect to the fact that the user is in motion becomes higher. Alternatively, for example, the position information of the information providing device 10 can be obtained and the movement score can be calculated based on the extent of variation in the position during a predetermined period of time. In that case, from the amount of variation in the position during a predetermined period of time, the speed can also be predicted and the transportation means such as a vehicle or walking can also be identified. Herein, although the degree of coincidence with respect to the state of being in motion is calculated, that is not the only possible case. Alternatively, for example, the degree of coincidence can be calculated with respect to the state of being in motion at a predetermined speed.

In this way, it can be said that, based on the acceleration information or the position information of the information providing device 10, the environment identifying unit 44 sets the information indicating the movement of the user U (herein, sets the movement score). However, in order to set the information indicating the movement of the user U, the environment identifying unit 44 is not limited to use the acceleration information and the position information, and can alternatively use arbitrary environment information. For example, the environment identifying unit 44 can use at least either the acceleration information or the position information.

Safety Scores

The environment identifying unit 44 calculates safety scores as the environment scores for the category indicating the safety of the user U. A safety score represents the information indicating the safety of the user U; and can be said to be the information indicating, in the form of a numerical value, whether the user U is present in a safe environment. The environment identifying unit 44 calculates the safety scores based on the environment information that, from among a plurality of types of environment information, is related to the safety of the user U. Examples of the environment information related to the safety of the user U include the surrounding image obtained by the camera 20A, the surrounding sound obtained by the microphone 20B, the intensity information of the light as detected by the light sensor 20F, the temperature information of the surrounding as detected by the temperature sensor 20G, and the humidity information of the surrounding as detected by the humidity sensor 20H.

More specifically, in the example illustrated in FIG. 5, the category indicating the safety of the user U includes a sub-category indicating a bright condition, a sub-category indicating that the infrared light or the ultraviolet light is at the appropriate level, a sub-category indicating that the temperature is at the appropriate level, a sub-category indicating that the humidity is at the appropriate level, and a sub-category indicating that a hazardous object is present. Regarding the sub-category indicating a bright condition, the environment identifying unit 44 calculates the safety score based on the intensity of the surrounding visible light as obtained by the light sensor 20F. The score for the sub-category indicating a bright condition can be said to be a numerical value indicating the degree of coincidence of the surrounding brightness with respect to a sufficient brightness level. In order to calculate the safety score for the sub-category indicating a bright condition, an arbitrary method can be implemented. For example, the safety score can be calculated based on the intensity of the visible light as detected by the light sensor 20F. Alternatively, the safety score for the sub-category indicating a bright condition can be calculated based on the luminance of the image taken by the camera 20A. Herein, although the degree of coincidence with respect to a sufficient brightness level is calculated, that is not the only possible case. Alternatively, the degree of coincidence with respect to an arbitrary brightness level can be calculated.

Regarding the sub-category indicating that the infrared light or the ultraviolet light is at the appropriate level, based on the intensity of the infrared light or the ultraviolet light as obtained by the light sensor 20F, the environment identifying unit 44 calculates the safety score for the sub-category indicating that the infrared light or the ultraviolet light is at the appropriate level. The safety score for the sub-category indicating that the infrared light or the ultraviolet light is at the appropriate level can be said to be a numerical value indicating the degree of coincidence of the intensity of the surrounding infrared light or the surrounding ultraviolet light with respect to the appropriate intensity of the infrared light or the ultralight light. Herein, an arbitrary method can be implemented for calculating the safety score for the sub-category indicating that the infrared light or the ultraviolet light is at the appropriate level. For example, the safety score can be calculated based on the intensity of the infrared light or the ultraviolet light as detected by the light sensor 20F. Herein, although the degree of coincidence with respect to the appropriate intensity of the infrared light or the ultraviolet light is calculated, that is not the only possible case. Alternatively, the degree of coincidence with respect to an arbitrary intensity of the infrared light or the ultraviolet light can be calculated.

Regarding the sub-category indicating that the temperature is at the appropriate level, the environment identifying unit calculates the safety score based on the surrounding temperature as obtained by the temperature sensor 20G. The safety score for the sub-category indicating that the temperature is at the appropriate level can be said to be a numerical value indicating the degree of coincidence of the surrounding temperature with respect to the appropriate temperature. Herein, an arbitrary method can be implemented for calculating the safety score for the sub-category indicating that the temperature is at the appropriate level. For example, the safety score can be calculated based on the surrounding temperature as detected by the temperature sensor 20G. Herein, although the degree of coincidence with respect to the appropriate temperature is calculated, that is not the only possible case. Alternatively, the degree of coincidence with respect to an arbitrary temperature can be calculated.

Regarding the sub-category indicating the humidity is at the appropriate level, the environment identifying unit 44 calculates the safety score based on the surrounding humidity as obtained by the humidity sensor 20H. The safety score for the sub-category indicating that the humidity is at the appropriate level can be said to be a numerical value indicating the degree of coincidence of the surrounding humidity with respect to the appropriate humidity. Herein, an arbitrary method can be implemented for calculating the safety score for the sub-category indicating that the humidity is at the appropriate level. For example, the safety score can be calculated based on the surrounding humidity as detected by the humidity sensor 20H. Herein, although the degree of coincidence with respect to the appropriate humidity is calculated, that is not the only possible case. Alternatively, the degree of coincidence with respect to an arbitrary humidity can be calculated.

Regarding the sub-category indicating that a hazardous object is present, the environment identifying unit 44 calculates the safety score based on the surrounding image obtained by the camera 20A. The safety score for the sub-category indicating that a hazardous object is present can be said to be a numerical value indicating the degree of coincidence with respect to the fact that a hazardous object is present. Herein, an arbitrary method can be implemented for calculating the safety score for the sub-category indicating that a hazardous object is present. For example, the determination can be performed in an identical manner to the abovementioned method in which, based on the surrounding image, it is determined whether a danger condition is present. That is, for example, the determination can be performed by determining whether the object captured in the surrounding image is a specific object. Moreover, regarding the sub-category indicating that a hazardous object is present, the environment identifying unit 44 calculates the safety score also based on the surrounding sound obtained by the microphone 20B. Herein, in order to calculate the safety score for the sub-category indicating that a hazardous object is present, an arbitrary method can be implemented. For example, the determination can be performed in an identical manner to the abovementioned method in which, based on the surrounding sound, it is determined whether a danger condition is present. That is, for example, the determination can be performed by determining whether the surrounding sound is a sound of a specific type.

Example of Environment Scores

In FIG. 5 is illustrated the environment scores calculated for environments D1 to D4. Each of the environments D1 to D4 corresponds to a different environment around the user U. In each of the environments D1 to D4, the environment score is calculated for each category (sub-category).

Meanwhile, the types of categories and subcategories illustrated in FIG. 5 are only exemplary, and the values of the environment scores in the environments D1 to D4 are also exemplary. Moreover, the information providing device 10 expresses the information indicating the environment around the user U in the form of a numerical value representing the environment score. Hence, it also becomes possible to take into account any error, and the environment around the user U can be estimated in a more accurate manner. In other words, it can be said that the information providing device 10 classifies the environment information into three or more degrees (herein, the environment scores), and can accurately estimate the environment around the user U. However, the information indicating the environment around the user U as set by the information providing device 10 based on the environment information is not limited to the values such as the environment scores, and can alternatively be data in an arbitrary format. For example, the information can be multiple-choice information indicating yes and no.

Deciding on Environment Pattern

From Step S16 to Step S22 illustrated in FIG. 4, the information providing device 10 calculates various environment scores according to the methods explained above. As illustrated in FIG. 4, after calculating the environment scores, based on each environment score, the information providing device 10 decides on an environment pattern indicating the environment around the user U (Step S24). That is, based on the environment scores, the environment identifying unit 44 determines the types of environments around the user U. On the one hand, the environment information and the environment scores represent the information indicating some of the factors of the environment around the user U that are detected by the environment sensor 20. On the other hand, the environment patterns can be said to represent indexes that are set based on the information indicating those factors and that comprehensively indicate the types of environments.

FIG. 6 is a table illustrating an example of the environment patterns. In the present embodiment, from among the environment patterns corresponding to various types of environments, the environment identifying unit 44 selects, based on the environment scores, the environment pattern matching with the environment around the user U. In the present embodiment, for example, the specification setting database 30C is used to store correspondence information (in the form of a table) in which the values of the environment scores are held in a corresponding manner to the environment patterns. Thus, based on the environment information and the correspondence information, the environment identifying unit 44 decides on the environment patterns. More particularly, from the correspondence information, the environment identifying unit 44 selects the environment patterns corresponding to the calculated values of the environment scores. In the example illustrated in FIG. 6, an environment pattern PT1 indicates that the user U is sitting in a train car; an environment pattern PT2 indicates that the user U is walking on a sidewalk; an environment pattern PT3 indicates that the user U is walking on a dark sidewalk; and an environment pattern PT4 indicates that the user U is doing shopping.

In the examples illustrated in FIGS. 5 and 6, in the environment D1, the environment score for “standing state” is equal to 10 and the environment score for “face orientation being in horizontal direction” is equal to 100. Hence, it can be predicted that the user U is seated and the face is oriented substantially in the horizontal direction. Moreover, since the environment score for “inside train car” is equal to 90, the environment score for “on railway track” is equal to 100, and the environment score for “sound inside train car” is equal to 90; it can be understood that the user U is present inside a train car. Moreover, since the environment score for “moving” is equal to 100, it can be understood that the user is moving at a uniform velocity or with acceleration. Furthermore, since the environment score for “bright” is equal to 50 and since it is the inside of a train car, it can be understood that it is darker than the outside. Moreover, since the environment scores for “infrared light/ultraviolet light at appropriate level”, “appropriate temperature”, and “appropriate humidity” are all equal to 100, it can be said that the situation is safe. Furthermore, since the environment score for “hazardous object present” is graphically equal to 10 and is auditorily equal to 20, it is possible to think that the situation is safe. That is, in the environment D1, according to the environment scores, it is possible to estimate that the user is seated on a seat while travelling in a train car and is in a safe and comfortable situation. The environment pattern of the environment D1 is treated as the environment pattern PT1 indicating the state of being seated in a train car.

Moreover, in the examples illustrated in FIGS. 5 and 6, in the environment D2, since the environment score for “the standing state” is equal to 10 and the environment score for “face orientation being in horizontal direction” is equal to 90, it can be predicted that the user U is seated and the face is oriented substantially in the horizontal direction. Moreover, since the environment score for “inside train car” is equal to 0, the environment score for “on railway track” is equal to 0, and the environment score for “sound inside train car” is equal to 10; it can be understood that the user U is not present in a train car. Herein, although not illustrated in the drawings, in the environment D2, based on the environment scores for the location, it can also be confirmed that the user U is on a road. Moreover, since the environment score for “moving” is equal to 100, it can be understood that the user is moving at a uniform velocity or with acceleration. Furthermore, since the environment score for “bright” is equal to 100, it can be understood that the user U is present outdoors in a bright condition. Moreover, since the environment score for “infrared light/ultraviolet light at appropriate level”, is equal to 80, it can be understood that the ultraviolet light has some impact. Furthermore, since the environment scores for “appropriate temperature” and “appropriate humidity” are equal to 100, it can be said that the situation is safe. Moreover, since the environment score for “hazardous object present” is graphically equal to 10 and is auditorily equal to 20, it is possible to think that the situation is safe. That is, in the environment D2, according to the environment scores, it is possible to estimate that the user is walking on a sidewalk, it is bright outdoors, and there is no indication of any hazardous objects. The environment pattern of the environment D2 is treated as the environment pattern PT2 indicating walking on a sidewalk. Moreover, in the examples illustrated in FIGS. 5 and 6, in the environment D3, the environment score for “standing state” is equal to 0 and the environment score for “face orientation being in horizontal direction” is equal to 90. Hence, it can be predicted that the user U is seated and the face is oriented substantially in the horizontal direction. Moreover, since the environment score for “inside train car” is equal to 5, the environment score for “on railway track” is equal to 0, and the environment score for “sound inside train car” is equal to 5; it can be understood that the user U is not present inside a train car. Meanwhile, although not illustrated in the drawings, in the environment D3, based on the environment score of the location, it can also be confirmed that user U is present on a road. Moreover, since the environment score for “moving” is equal to 100, it can be understood that the user is moving at a uniform velocity or with acceleration. Furthermore, since the environment score for “bright” is equal to 10, it can be understood that it is a dark environment. Moreover, since the environment scores for “infrared light/ultraviolet light at appropriate level” is equal to 100, it can be said that the situation is safe. Furthermore, since the environment score for “appropriate temperature” is equal to 75, it can be said that it is hotter or colder than the standard level. Moreover, since the environment score for “hazardous object present” is graphically equal to 90 and is auditorily equal to 80, it can be understood that something is approaching while making a sound. Furthermore, although not illustrated in the drawings, it is possible to determine the object from the sound and the video. Herein, it is possible to determine that a vehicle is approaching from the anterior side, and the sound is of the engine of the vehicle. That is, in the environment D3, it can be estimated from the environment scores that the user U is walking on a dark sidewalk on the outside and that a vehicle representing a hazardous object is approaching. The environment pattern of the environment D3 is treated as the environment pattern PT3 indicating walking on a dark sidewalk.

Moreover, in the examples illustrated in FIGS. 5 and 6, in the environment D4, the environment score for “standing state” is equal to 0 and the environment score for “face orientation being in horizontal direction” is equal to 90. Hence, it can be predicted that the user U is seated and the face is oriented substantially in the horizontal direction. Moreover, since the environment score for “inside train car” is equal to 20, the environment score for “on railway track” is equal to 0, and the environment score for “sound inside train car” is equal to 5; it can be understood that the user U is not present inside a train. Meanwhile, although not illustrated in the drawings, in the environment D3, based on the environment score of the location, it can also be confirmed that user U is present in a shopping center. Moreover, since the environment score for "moving" is equal to 80, it can be understood that the user is moving around gently. Furthermore, since the environment score for "bright" is equal to 70, it can be predicted that it is relatively bright and the brightness is about equal to indoor illumination. Moreover, since the environment scores for "infrared light/ultraviolet light at appropriate level" is equal to 100, it can be said that the situation is safe. Furthermore, since the environment score for "appropriate temperature" is equal to 100, it is a comfortable environment. However, since the environment score for "appropriate humidity" is equal to 90, it is not really possible to say that the environment is comfortable. Moreover, since the environment score for "hazardous object present" is graphically equal to 10 and is auditorily equal to 20, it is possible to think that the situation is safe. That is, in the environment D4, it can be estimated from the environment scores that the user U is walking in a shopping center with a relatively bright surrounding and without any hazardous objects. The environment pattern of the environment D4 is treated as the environment pattern PT4 indicating the state of doing shopping.

Setting of Target Device and Reference Output Specification

After the environment pattern is selected, in the information providing device 10, based on the environment pattern, the output selecting unit 48 and the output specification deciding unit 50 decide on the target device to be operated in the output unit 26, and set the reference output specification (Step S26).

Setting of Target Device

As explained above, a target device is a device to be operated from among the devices in the output unit 26. In the present embodiment, based on the environment information, more desirably, based on the environment pattern, the output selecting unit 48 selects the target device from among the display unit 26A, the sound output unit 26B, and the sensory stimulus output unit 26C. The environment pattern represents the information indicating the current environment around the user U. Hence, as a result of selecting the target device based on the environment pattern, it becomes possible to select an appropriate sensory stimulus corresponding to the current environment around the user U.

For example, based on the environment information, the output selecting unit 48 determines whether it is highly necessary for the user U to visually confirm the surrounding environment and, based on that determination result, can determine whether to treat the display unit 26A as the target device. In that case, for example, if the necessity to visually confirm the surrounding environment is lower than a predetermined level, then the output specification deciding unit 50 can select the display unit 26A as the target device. On the other hand, if the necessity is equal to or higher than the predetermined level, then the output specification deciding unit 50 does not select the display unit 26A as the target device. The determination about whether it is necessary for the user U to visually confirm the surrounding environment can be performed in an arbitrary manner. For example, when the user U is in motion or when a hazardous object is present, it can be determined that the necessity is equal to or higher than the predetermined level.

Moreover, for example, based on the environment information, the output selecting unit 48 determines whether it is highly necessary for the user U to listen to the sounds of the surrounding environment and, based on that determination result, can determine whether to treat the sound output unit 26B as the target device. In that case, for example, if the necessity to listen to the sounds of the surrounding environment is lower than a predetermined level, then the output specification deciding unit 50 can select the sound output unit 26B as the target device. On the other hand, if the necessity is equal to or higher than the predetermined level, then the output specification deciding unit 50 does not select the sound output unit 26B as the target device. The determination about whether it is necessary for the user U to listen to the sounds of the surrounding environment can be performed in an arbitrary manner. For example, when the user U is in motion or when a hazardous object is present, it can be determined that the necessity is equal to or higher than the predetermined level.

Furthermore, for example, based on the environment information, the output selecting unit 48 determines whether the user U is in a position to receive a tactile stimulus and, based on that determination result, can determine whether to treat the sensory stimulus output unit 26C as the target device. In that case, for example, if it is determined that the user is in a position to receive a tactile stimulus, then the output specification deciding unit 50 selects the sensory stimulus output unit 26C as the target device. On the other hand, if it is determined that the user is in no position to receive a tactile stimulus, then the output specification deciding unit 50 does not select the sensory stimulus output unit 26C as the target device. The determination about whether the user U is in a position to receive a tactile stimulus can be performed in an arbitrary manner. For example, when the user U is in motion or when a hazardous object is present, it can be determined that the user U is in no position to receive a tactile stimulus.

Till now, the explanation was given about the methods by which the output selecting unit 48 selects the target device. More particularly, for example, it is desirable that the output selecting unit 48 selects the target device based on a table indicating the relationship between the environment patterns and the target devices as illustrated in FIG. 8 (explained later).

Setting of Reference Output Specification

Based on the environment information, more desirably, based on the environment pattern, the output specification deciding unit 50 decides on the reference output specification. An output specification represents an index about the manner of outputting a stimulus that is output by the output unit 26. For example, the output specification of the display unit 26A indicates the manner of displaying the content image PS that is output, and can also be termed as the display specification. Examples of the output specification of the display unit 26A include the size (dimensions) of the content image PS, the degree of transparency of the content image PS, and the display details (content) of the content image PS. The size of the content image PS indicates the dimensions of the content image PS that occupy the screen of the display unit 26A. The degree of transparency of the content image PS indicates the extent to which the content image PS is transparent. Herein, higher the degree of transparency of the content image PS, the greater amount of light falling as the environmental image PA on the eyes of the user U passes through the content image PS. With that, the environmental image PA that is superimposed on the content image PS becomes more clearly visible. In this way, it can be said that, based on the environment pattern, the output specification deciding unit 50 decides on the size, the degree of transparency, and the display details of the content image PS as the output specification of the display unit 26A. However, the output specification of the display unit 26A need not always include the size, the degree of transparency, as well as the display details of the content image PS. For example, the output specification of the display unit 26A can include at least either the size, or the degree of transparency, or the display details of the content image PS; or can include some other information.

For example, the output specification deciding unit 50 can determine, based on the environment information, whether it is necessary for the user U to visually confirm the surrounding environment; and, based on that determination result, can decide on the output specification of the display unit 26A (the reference output specification). In that case, the output specification deciding unit 50 decides on the output specification of the display unit 26A (the reference output specification) in such a way that the degree of visibility of the environmental image PM increases in proportion to the necessity to visually confirm of the surrounding environment. The degree of visibility indicates the ease of visual confirmation of the environmental image PM. For example, in proportion to the necessity of visual confirmation of the surrounding environment, the output specification deciding unit 50 can reduce the size of the content image PS, or can increase the degree of transparency of the content image PS, or can increase the restrictions on the display details of the content image PS, or can implement such changes in combination. Meanwhile, in order to increase the restrictions on the display details of the content image PS; for example, distribution images can be excluded from the display details, and the display details can be set to at least either navigation images or notification images. Meanwhile, the determination about whether it is necessary for the user U to visually confirm the surrounding environment can be performed in an arbitrary manner. For example, when the user U is moving or when a hazardous object is present, it can be determined that the user U needs to visually confirm the surrounding environment.

Figure 7:
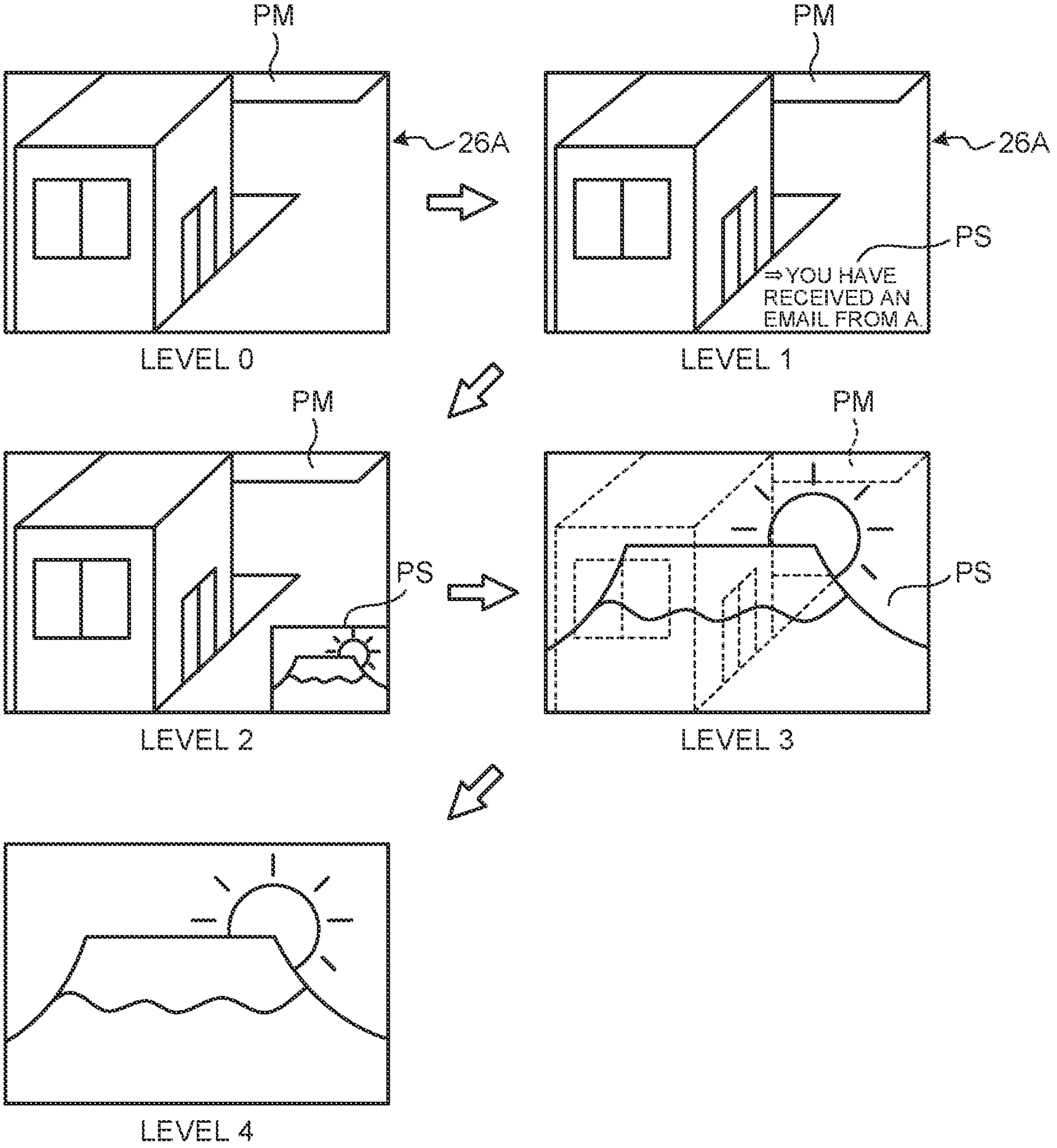
FIG. 7 is a schematic diagram for explaining an example of the levels of the output specification of a content image.

FIG. 7 is a schematic diagram for explaining an example of the levels of the output specification of a content image. In the present embodiment, the output specification deciding unit 50 can classify the output specification of the content image PS into different levels and can select the level of the output specification based on the environment information. In that case, the output specification of the content image PS is set in such a way that the degree of visibility of the environmental image PM is different for each level. In the present embodiment, the levels of the output specification are set in such a way that, higher the level, the stronger becomes the output stimulus and the lower becomes the degree of visibility of the environmental image PM. For that reason, the output specification deciding unit 50 sets the levels of the output specification in inverse proportion to the necessity to visually confirm the surrounding environment. In the example illustrated in FIG. 7, at a level 0, the content image PS is not displayed and only the environmental image PM is visually confirmed. Hence, the degree of visibility of the environmental image PM becomes equal to the maximum level.

As illustrated in FIG. 7, at a level 1, although the content image PS is displayed, there is restriction on the display details thereof. Herein, distribution images are excluded from the display details, and the display details are set to at least either navigation images or notification images. Moreover, at the level 1, the size of the content image PS is set to be small. At the level 1, only when it becomes necessary to display a navigation image or a notification image, the content image PS is displayed in a superimposed manner on the environmental image PM. Thus, at the level 1, due to the display of the content image PM, the degree of visibility of the environmental image PM is lower than the degree of visibility thereof at the level 0. However, since there is restriction on the display details of the content image PS, the degree of visibility is still on the higher side.

As illustrated in FIG. 7, at a level 2, although there is no restriction on the display details of the content image PS, the size of the content image PS is restricted to be small. As compared to the degree of visibility at the level 1, the degree of visibility at the level 2 is lower because there are no restrictions on the display details.

As illustrated in FIG. 7, at a level 3, there is no restriction on the display details and the size of the content image PS; and, for example, the content image PS is displayed over the entire screen of the display unit 26A. However, at the level 3, the degree of transparency of the content image PS is restricted to be high. Hence, at the level 3, the semitransparent content image PS is visually confirmed along with the environmental image PM that is superimposed on the content image PS. As compared to the degree of visibility of the environmental image PM at the level 2, the degree of visibility at the level 3 is lower because there is no restriction on the size of the content image PS.

As illustrated in FIG. 7, at a level 4, there is no restriction on the display details, the size, and the degree of transparency of the content image PS; and, for example, the content image PS is displayed in such a way that the degree of transparency becomes equal to zero over the entire screen of the display unit 26A. At the level 4, since the degree of transparency of the content image PS is equal to zero (indicating a nontransparent image), the environmental image PM is not visually confirmed and only the content image PS is confirmed. For that reason, at the level 4, the degree of visibility of the environmental image PM becomes the lowest. Meanwhile, at the level 4, for example, the image present within the field of view of the user U can be displayed as the environmental image PM in some region at one end of the screen of the display unit 26A.

Till now, the explanation was given about the output specification of the display unit 26A. Similarly, the output specification deciding unit 50 decides on the output specification also of the sound output unit 26B and the sensory stimulus output unit 26. Examples of the output specification of the sound output unit 26B (the sound specification) include the sound volume, the presence or absence of the acoustic, and the extent of the acoustic. Herein, the acoustic indicates special effects such as the surround sound or the stereophonic sound field. Thus, higher the sound volume or greater the extent of the acoustic, the stronger can be the auditory stimulus given to the user. For example, based on the environment information, the output specification deciding unit 50 decides whether it is necessary for the user U to listen to the surrounding sound and, based on that determination result, can decide on the output specification of the sound output unit 26B (the reference output specification). In that case, the output specification deciding unit 50 decides on the output specification of the sound output unit 26B (the reference output specification) in such a way that the sound volume and the extent of the acoustic increases in inverse proportion to the necessity to listen to the surrounding sound. The determination about whether it is necessary for the user U to listen to the surrounding sound can be performed in an arbitrary manner. For example, when the user U is in motion or when a hazardous object is present, it can be determined that the user U needs to listen to the surrounding sound. Meanwhile, in an identical manner to the output specification of the display unit 26A, the output specification deciding unit 50 can set levels regarding the output specification of the sound output unit 26B.

Regarding the sensory stimulus output unit 26C, the intensity of the tactile stimulus or the frequency of outputting the tactile stimulus can be treated as the output specification. Higher the intensity of the tactile stimulus or higher the frequency of the tactile stimulus, the more intense can be the degree of the tactile stimulus given to the user U. For example, based on the environment information, the output specification deciding unit 50 determines whether the user U is in a position to receive a tactile stimulus and, based on that determination result, can determine the output specification of the sensory stimulus output unit 26C (the reference output specification). In that case, the output specification deciding unit 50 decides on the output specification of the sensory stimulus output unit 26C (the reference output specification) in such a way that, higher the suitability to receive the tactile stimulation, the higher becomes the intensity of the tactile stimulus or the higher becomes the frequency of the tactile stimulus. The determination about whether the user U is in a position to receive a tactile stimulus can be performed in an arbitrary manner. For example, when the user U is in motion or when a hazardous object is present, it can be determined that the user U is in a position to receive a tactile stimulus. Meanwhile, in an identical manner to the output specification of the display unit 26A, the output specification deciding unit 50 can set levels regarding the output specification of the sensory stimulus output unit 26C.

Specific Example of Setting of Target Device and Reference Output Specification

It is desirable that the output selecting unit 48 and the output specification deciding unit 50 decide on the target device and the reference output specification based on the relationship of the environment patterns with the target devices and the reference output specifications. FIG. 8 is a table indicating the relationship of the environment patterns with the target devices and the reference output specifications. Thus, based on relationship information indicating the relationship of the environment patterns with the target devices and the reference output specifications, the output selecting unit 48 and the output specification deciding unit 50 decide on the target device and the reference output specification. The relationship information represents information (in the form of a table) in which the environment patterns are stored in a corresponding manner to the target devices and the reference output specifications. The relationship information is stored in, for example, the specification setting database 30C. In the relationship information, the reference output specification is set regarding each device of the output unit 26, that is, regarding each of the display unit 26A, the sound output unit 26B, and the sensory stimulus output unit 26C. Based on such relationship information and based on the environment pattern set by the environment identifying unit 44, the output selecting unit 48 and the output specification deciding unit 50 decide on the target device and the reference output specification. More particularly, the output selecting unit 48 and the output specification deciding unit 50 read the relationship information; select, from the relationship information, the target device and the reference output specification corresponding to the environment pattern set by the environment identifying unit 44; and decide on the target device and the reference output specification.

In the example illustrated in FIG. 8, with respect to the environment pattern PT1 indicating the state of being seated in a train car; all of the display unit 26A, the sound output unit 26B, and the sensory stimulus output unit 26C are treated as the target devices, and the level of the respective reference output specifications is set to the level 4. Herein, higher the level, the higher is the output stimulus. Moreover, with respect to the environment pattern PT2 indicating walking on a sidewalk, although the situation is almost safe and comfortable, it is believed that paying attention in the anterior direction is necessary while walking. Hence, although all of the display unit 26A, the sound output unit 26B, and the sensory stimulus output unit 26C are treated as the target devices; the level of the respective reference output specifications is set to the level 3. Furthermore, with respect to the environment pattern PT3 indicating walking on a dark sidewalk, it cannot be said to be a safe situation. Hence, in order to ensure that attention is paid in the anterior direction and that the outside sounds are properly heard; only the sound output unit 26B and the sensory stimulus output unit 26C are treated as the target devices, and the levels of the reference output specification of the display unit 26A, the sound output unit 26B, and the sensory stimulus output unit 26C are set to the level 0, the level 2, and the level 2, respectively. Moreover, with respect to the environment pattern PT4 indicating the state of doing shopping, although the situation is almost safe, it is assumed that information causing distraction need not be provided. Hence, although all of the display unit 26A, the sound output unit 26B, and the sensory stimulus output unit 26C are treated as the target devices; the level of the respective reference output specifications is set to the level 2. Meanwhile, with reference to FIG. 8, the setting of the target device and the reference output specification for each environment pattern is only exemplary, and can be set in an appropriate manner.

In this way, in the present embodiment, based on the preset relationship of the environment patterns with the target devices and the reference output specifications, the information providing device 10 sets the target device and the reference output specification. However, the method for setting the target device and the reference output specification is not limited to the method explained above. Alternatively, based on the environment information detected by the environment sensor 20, the information providing device 10 can set the target device and the reference output specification according to an arbitrary method. Meanwhile, the information providing device 10 need not select the target device as well as the reference output specification based on the environment information, and can alternatively select least either the target device or the reference output specification.

Obtaining Biological Information

Figure 9:
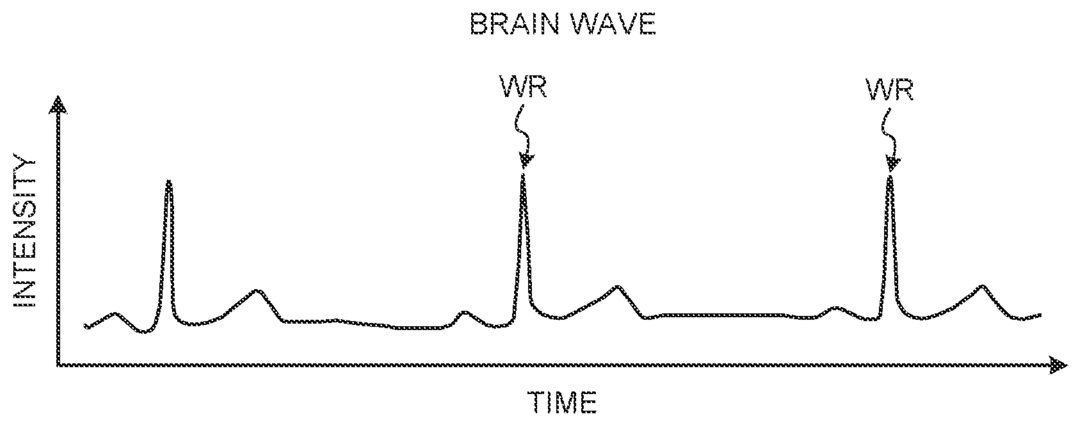
FIG. 9 is a graph illustrating an example of a pulse wave.

As illustrated in FIG. 4, in the information providing device 10, the biological information obtaining unit 42 obtains the biological information of the user U as detected by the biological sensor 22 (Step S28). The biological information obtaining unit 42 obtains the pulse wave information of the user U from the pulse wave sensor 22A, and obtains the brain wave information of the user U from the brain wave sensor 22B. FIG. 9 is a graph illustrating an example of a pulse wave. As illustrated in FIG. 9, a pulse wave is a waveform in which a peak called an R-wave WR appears at regular intervals. The heart is controlled by the autonomic nervous system, and the pulse rate results in the generation, at the cell level, of electric signals that represent the trigger for getting the heart pumping. Usually, the heart rate increases when adrenaline is released due to the sympathomimetic effect, and decreases when acetylcholine is released due to the parasympathomimetic effect. According to "Evaluation of diabetic autonomic nerve damage using power spectrum analysis of R-R interval of electrocardiogram" (in Japanese) by Nobuyuki Ueda (Clinical Diabetes 35(1): 17-23, 1992), it is believed that the function of the autonomic nerves is understood by checking the variation in the R-R interval in the temporal waveform of a pulse wave as illustrated in FIG. 9. The R-R interval represents the interval between chronologically successive R-waves WR. At the cell level, the cardiac electrical activity indicates repetition of depolarization/action potential and repolarization/resting potential, and the detection of such cardiac electrical activity from the body surface enables detection of an electrocardiogram. Meanwhile, the speed of propagation of the pulse waves is very high, and they get propagated throughout the body almost simultaneously to the beating of the heart. Hence, it can be said that the heartbeats are in synchronization also with the pulse waves. Since the pulse waves of the heartbeat and the R-waves of an electrocardiogram are in synchronization, the R-R interval of the pulse waves can be treated to be equivalent to the R-R interval of an electrocardiogram. The fluctuation in the R-R interval of a pulse wave can also be considered as the derivative with respect to time. Hence, if the derivative value is calculated and the magnitude of the fluctuation is detected; then, regardless of the intention of the concerned person, it becomes possible to predict, to a certain extent, the degree of activation or the degree of deactivation of the autonomic nerves, that is, to predict any frustration attributed to the tumult, or the sense of discomfort in an overcrowded train car, or the stress occurring in a relatively shorter period of time.

On the other hand, regarding the brain waves, the waves such as the a waves and the β waves can be detected or the activity of the basic pattern (background brain waves) can be detected, and that can be followed by detecting the amplitude of the activity. With that, it becomes possible to predict, to a certain extent, the fact that the activity of the entire brain is in a heightened state or in a declined state. For example, from the degree of activation of the prefrontal region of the brain, it becomes possible to understand the degree of interest, such as how much interest is taken in an object about which a visual stimulus is given.

Identification of User State and Calculation of Output Specification Correction Degree As illustrated in FIG. 4, in the information providing device 10, after the biological information is obtained, based on the biological information of the user U, the user state identifying unit 46 identifies the user state indicating the mental state of the user U; and then calculates an output specification correction degree based on the user state (Step S30). The output specification correction degree is a value meant for correcting the reference output specification that is set by the output specification deciding unit 50. Then, based on the reference output specification and the output specification correction degree, the final output specification is decided.

FIG. 10 is a table illustrating an example of the relationship between the user states and the output specification correction degrees. In the present embodiment, based on the brain wave information of the user U, the user state identifying unit 46 identifies the cerebral activation degree of the user U as the user state. Herein, based on the brain wave information of the user U, the user state identifying unit 46 can identify the cerebral activation degree according to an arbitrary method. For example, the cerebral activation degree can be identified from a specific frequency domain with respect to the waveforms of the α waves and the β waves. In that case, for example, the user state identifying unit 46 performs fast Fourier transform of the temporal waveform of the brain waves, and calculates the power spectrum quantity of the high-frequency portion of the a waves (for example, 10 Hz to 11.75 Hz). If the power spectrum quantity of the high-frequency portion of the α waves is large, then it can be predicted that the user U is relaxed and extremely focused at the same time. The user state identifying unit 46 determines that the cerebral activation degree is high in proportion to the power spectrum quantity of the high-frequency portion of the a waves. When the power spectrum quantity of the high-frequency portion of the α waves is within a predetermined numerical range, the user state identifying unit 46 sets the cerebral activation degree as VA3. Moreover, when the power spectrum quantity of the high-frequency portion of the a waves is within a predetermined numerical range that is lower than the numerical range for the cerebral activation degree VA3, the user state identifying unit 46 sets the cerebral activation degree as VA2. Furthermore, when the power spectrum quantity of the high-frequency portion of the α waves is within a predetermined numerical range that is lower than the numerical range for the cerebral activation degree VA2, the user state identifying unit 46 sets the cerebral activation degree as VA1. Herein, the cerebral activation degree is assumed to be in ascending order of VA1, VA2, and VA3. Regarding the high-frequency components of the β waves (for example, 18 Hz to 29.75 Hz), greater the power spectrum quantity, the higher is the possibility of exercising psychological "caution" or experiencing "perturbation". Hence, the cerebral activity degree can be identified also using the power spectrum quantity of the high-frequency components of the β waves.

The user state identifying unit 46 decides on the output specification correction degree based on the cerebral activity degree of the user U. In the present embodiment, the output specification correction degree is decided based on output specification correction degree relationship information indicating the relationship between the user state (in this example, the cerebral activity degree) and the output specification correction degree. The output specification correction degree relationship information represents information (in the form of a table) in which the user states are stored in a corresponding manner to the output specification correction degrees. For example, the output specification correction degree relationship information is stored in the specification setting database 30C. In the output specification correction degree relationship information, the output specification correction degrees are set for each device included in the output unit 26, that is, for each of the display unit 26A, the sound output unit 26B, and the sensory stimulus output unit 26C. Thus, the user state identifying unit 46 decides on the output specification correction degree based on the output specification correction degree relationship information and the identified user state. More particularly, the user state identifying unit 46 reads the output specification correction degree relationship information; selects, from the output specification correction degree relationship information, the output specification correction degree corresponding to the set cerebral activity degree of the user U; and decides on the output specification correction degree. In the example illustrated in FIG. 10, as far as the cerebral activity degree VA3 is concerned, the output specification correction degree for each of the display unit 26A, the sound output unit 26B, and the sensory stimulus output unit 26C is set to −1. As far as the cerebral activity degree VA2 is concerned, the output specification correction degree for each of the display unit 26A, the sound output unit 26B, and the sensory stimulus output unit 26C is set to 0. As far as the cerebral activity degree VA1 is concerned, the output specification correction degree for each of the display unit 26A, the sound output unit 26B, and the sensory stimulus output unit 26C is set to 1. Herein, higher the set value of the output specification correction degree, the higher is the output specification. That is, the user state identifying unit 46 sets the output specification correction degree in such a way that the output specification is set to be higher in inverse proportion to the cerebral activity degree. Herein, setting the output specification to a higher level implies increasing the intensity of a sensory stimulus. The same meaning is applied in the following explanation too. Meanwhile, the values of the output specification correction degrees illustrated in FIG. 10 are only exemplary, and can be set in an appropriate manner.

Moreover, based on the pulse wave information of the user U, the user state identifying unit 46 identifies the mental balance degree of the user U as the user state. In the present embodiment, from the brain wave information, the user state identifying unit 46 calculates the fluctuation value of the interval of chronologically successive R-waves WH, that is, calculates the derivative value of the R-R interval; and identifies the cerebral activity degree of the user U based on the derivative value of the R-R interval. Herein, smaller the derivative value of the R-R interval, that is, lesser the fluctuation in the interval of the R-waves WH, the higher is the mental balance degree of the user U as identified by the user state identifying unit 46. In the example illustrated in FIG. 10, from the pulse wave information of the user U, the user state identifying unit 46 classifies the mental balance degree into one of VB3, VB2, and VB1. When the derivative value of the R-R interval is within a predetermined numerical range, the user state identifying unit 46 sets the mental balance degree as VB3. When the derivative value of the R-R interval is within a predetermined numerical range that is higher than the numerical range for the mental balance degree VB3, the user state identifying unit 46 sets the mental balance degree as VB2. When the derivative value of the R-R interval is within a predetermined numerical range that is lower than the numerical range for the mental balance degree VB2, the user state identifying unit 46 sets the mental balance degree as VB1. Herein, the mental balance degree is assumed to be in ascending order of VB1, VB2, and VB3.

The user state identifying unit 46 decides on the output specification correction degree based on the output specification correction degree relationship information and the identified mental balance degree. More particularly, the user state identifying unit 46 reads the output specification correction degree relationship information; selects, from the output specification correction degree relationship information, the output specification correction degree corresponding to the set mental balance degree of the user U; and decides on the output specification correction degree. In the example illustrated in FIG. 10, as far as the mental balance degree VB3 is concerned, the output specification correction degree for each of the display unit 26A, the sound output unit 26B, and the sensory stimulus output unit 26C is set to 1. As far as the mental balance degree VB2 is concerned, the output specification correction degree for each of the display unit 26A, the sound output unit 26B, and the sensory stimulus output unit 26C is set to 0. As far as the mental balance degree VB1 is concerned, the output specification correction degree for each of the display unit 26A, the sound output unit 26B, and the sensory stimulus output unit 26C is set to −1. That is, the user state identifying unit 46 sets the output specification correction degree in such a way that the output specification (sensory stimulus) is set to be higher in proportion to the mental balance degree. Meanwhile, the values of the output specification correction degrees illustrated in FIG. 10 are only exemplary, and can be set in an appropriate manner.

In this way, based on the preset relationship between the user states and the output specification correction degrees, the user state identifying unit 46 sets the output specification correction degrees. However, that is not the only possible method for setting the output specification correction degrees. Alternatively, the information providing device 10 can set the output specification correction degrees according to an arbitrary method based on the biological information detected by the biological sensor 22. Moreover, the information providing device 10 calculates the output specification correction degrees using the cerebral activation degree identified from the brain waves as well as using the mental balance degree identified from the pulse waves. However, that is not the only possible case. Alternatively, for example, the information providing device 10 can calculate the output specification correction degrees either using the cerebral activation degree identified from the brain waves or using the mental balance degree identified from the pulse waves. Furthermore, the information providing device 10 treats the biological information as numerical values, and estimates the user state based on the biological information. Hence, the error in the biological information can also be reflected, thereby making it possible to estimate the mental state of the user U with more accuracy. In other words, it can be said that the information providing device 10 classifies the biological information or classifies the user state based on the biological information into one of three or more degrees, and thus can estimate the mental state of the user U with more accuracy. However, the information providing device 10 is not limited to classify the biological information or classify the user state based on the biological information into one of three or more degrees. Alternatively, for example, the biological information or the user state based on the biological information can be multiple-choice information indicating yes and no.

Generation of Output Restriction Necessity Information

As illustrated in FIG. 4, in the information providing device 10, the user state identifying unit 46 generates output restriction necessity information based on the biological information of the user U (Step S32). FIG. 11 is a table illustrating an example of the output restriction necessity information. The output restriction necessity information indicates whether the output restriction on the output unit 26 is necessary, and can be said to be the information indicating whether or not to allow the operation of the output unit 26. The output restriction necessity information is generated for each device included in the output unit 26A, that is, for each of the display unit 26A, the sound output unit 26B, and the sensory stimulus output unit 26C. In other words, regarding each of the display unit 26A, the sound output unit 26B, and the sensory stimulus output unit 26C; the user state identifying unit 46 generates, based on the biological information, output restriction necessity information indicating whether or not to allow the operation of the concerned device. More particularly, the user state identifying unit 46 generates output restriction necessity information based on the biological information as well as the environment information. Thus, the user state identifying unit 46 generates output restriction necessity information based on: the user state that is set based on the biological information; and the environment score that is calculated based on the environment information. In the example illustrated in FIG. 11, the user state identifying unit 46 generates output restriction necessity information based on the cerebral activation degree representing the user state and based on the location score with respect to the sub-category indicating "on railway track" that represents an environment score. In the example illustrated in FIG. 11, when a first condition is satisfied in which the location score is equal to 100 with respect to the sub-category indicating "on railway track" and in which the cerebral activity degrees are set to VA3 and VA2, the user state identifying unit 46 generates output restriction necessity information that indicates non-authorization for using the display unit 26A. Meanwhile, the first condition is not limited to the case in which the location score is equal to 100 with respect to the sub-category indicating "on railway track" and in which the cerebral activity degrees are set to VA3 and VA2. Alternatively, for example, in the first condition can be set to the case in which the position of the information providing device 10 is within a predetermined area and in which the cerebral activity degree is equal to or lower than a cerebral activity degree threshold value. Herein, the predetermined area is, for example, on the railway track or on a road.

Moreover, in the example illustrated in FIG. 11, the user state identifying unit 46 generates output restriction necessity information based on: the cerebral activation degree representing the user state; and the movement score for the sub-category indicating "moving". In the example illustrated in FIG. 11, when a first condition is satisfied in which the movement score is equal to 0 for the sub-category indicating "moving" and in which the cerebral activity degrees are set to VA3 and VA2, the user state identifying unit 46 generates output restriction necessity information that indicates non-authorization for using the display unit 26A. Meanwhile, the second condition is not limited to the case in which the movement score is equal to 0 for the sub-category indicating "moving" and in which the cerebral activity degrees are set to VA3 and VA2. Alternatively, for example, the second condition can be set to the case in which the variation in the position of the information providing device 10 per unit time is equal to or smaller than a predetermined variation threshold value and in which the cerebral activation degree is equal to or lower than a cerebral activity degree threshold value.

In this way, when the biological information and the environment information satisfies a specific relationship, that is, when the user state and the environment score satisfy at least either the first condition or the second condition, the user state identifying unit 46 generates output restriction necessity information indicating non-authorization for using the display unit 26A. On the other hand, if the user state and the environment score neither satisfy the first condition nor satisfy the second condition, then the user state identifying unit 46 does not generate output restriction necessity information indicating non-authorization for using the display unit 26A, and generates output restriction necessity information indicating authorization for using the display unit 26A. Meanwhile, the generation of output restriction necessity information is not a mandatory operation.

Acquisition of Content Image

As illustrated in FIG. 4, in the information providing device 10, the content image obtaining unit 52 obtains image data of the content image PS (Step S34). The image data of the content image PS represents image data meant for displaying the content (display details) of content images. The content image obtaining unit 52 obtains the image data of content images from an external device via the content image receiving unit 28A.

Meanwhile, the content image obtaining unit 52 can obtain the image data of the content image of the content (the display details) corresponding to the position (the global coordinates) of the information providing device 10 (the user U). The position of the information providing device 10 is identified by the GNSS receiver 20C. For example, when the user U is present within a predetermined range from a particular position, the content image obtaining unit 52 receives the content related to that position. In principle, the display of the content image PS can be controlled according to the intention of the user U. However, when the display setting is done to allow the display, the place or the timing of display is not known. Hence, although the display is a convenient means, it sometimes can cause nuisance. In that regard, the specification setting database 30C can be used to record the information indicating the display authorization/non-authorization or the display specification of the content image PS as set by the user U. The content image obtaining unit 52 reads that information from the specification setting database 30C and, based on that information, controls the acquisition of the content image PS. Alternatively, same information as the position information and the specification setting database 30C can be maintained at an Internet site, and the content image obtaining unit 52 can control the acquisition of the content image PS while checking the maintained details. Meanwhile, the operation performed at Step S34 for obtaining the image data of the content image PS is not limited to be executed before the operation performed at Step S36 (explained later). Alternatively, the operation can be performed at an arbitrary timing before the operation at Step S38 (explained later) is performed.

Meanwhile, along with obtaining the image data of the content image PS, the content image obtaining unit 52 can also obtain the sound data and the tactile stimulus data related to the content image PS. The sound output unit 26B outputs the sound data related to the content image PS as the sound content (the details of the sound), and the sensory stimulus output unit 26C outputs the tactile stimulus data related to the content image PS as the tactile stimulus content (the details of the tactile stimulus).

Setting of Output Specification

Subsequently, as illustrated in FIG. 4, in the information providing device 10, the output specification deciding unit 50 decides on the output specification based on the reference output specification and the output specification correction degree (Step S36). The output specification deciding unit 50 corrects the reference output specification, which is set based on the environment information, according to the output specification correction degree set based on the biological information; and decides on the final output specification for the output unit 26. Herein, an arbitrary formula can be used for correcting the reference output specification according to the output specification correction degree.

As explained above, the information providing device 10 corrects the reference output specification, which is set based on the environment information, according to the output specification correction degree set based on the biological information; and decides on the final output specification. However, the information providing device 10 is not limited to decide on the output specification by correcting the reference output specification according to the output specification correction degree. Alternatively, the output specification can be decided according to an arbitrary method using at least either the environment information or the biological information. That is, the information providing device 10 either can decide on the output specification according to an arbitrary method based on the environment information and the biological information, or can decide on the output specification according to an arbitrary method based on either the environment information or the biological information. For example, based on the environment information from among the environment information and the biological information, the information providing device 10 can decide on the output specification using the method explained earlier in regard to deciding on the reference output specification. Alternatively, based on the biological information from among the environment information and the biological information, the information providing device 10 can decide on the output specification using the method explained earlier in regard to deciding on the output specification correction degree.

Meanwhile, at Step S32, when output restriction necessity information indicating non-authorization for using the output unit 26 is generated, the output selecting unit 48 selects the target device not based on the environment score but based on the output restriction necessity information. That is, at Step S26, even if the output unit 26 has been selected as the target device based on the environment score, if the specification is not authorized in the output restriction necessity information, that output unit 26 is not considered as the target device. In other words, the output selecting unit 48 selects the target device based on the output restriction necessity information and the environment information. Moreover, since the output restriction necessity information is set based on the biological information, the target device can be said to be set based on the biological information and the environment information. However, the output selecting unit 48 is not limited to select the target device based on the biological information as well as the environment information. Alternatively, the output selecting unit 48 can select the target device based on at least either the biological information or the environment information.

Output Control

After the target device and the output specification is set and after the image data of the content image PS is obtained; as illustrated in FIG. 4, in the information providing device 10, the output control unit 54 causes the target device to perform output based on the output specification (Step S38). The output control unit 54 does not operate the output unit 26 that is not selected as the target device.

For example, when the display unit 26A is set as the target device, the output control unit 54 displays, in the display unit 26A and according to the output specification of the display unit 26A, the content image PS that is based on the content image data obtained by the content image obtaining unit 52. As explained earlier, the output specification is set based on the environment information and the biological information. As a result of displaying the content image PS according to the output specification, the content image PS can be displayed in an appropriate form corresponding to the environment around the user U and the mental state of the user U.

When the sound output unit 26B is set as the target device, the output control unit 54 outputs, to the sound output unit 26B and according to the output specification of the sound output unit 26B, sounds based on the sound data obtained by the content image obtaining unit 52. In that case too, for example, the intensity of the auditory stimulus can be lowered in inverse proportion to the cerebral activation degree of the user U or in proportion to the mental balance degree of the user U. With that, when the user U is focused in some other thing or does not have enough mental space, the risk of being bothered by the sounds can be lowered. On the other hand, the intensity of the auditory stimulus can be increased in inverse proportion to the cerebral activation degree of the user U or in proportion to the mental balance degree of the user U. With that, the user U becomes able to obtain information from the sounds in an appropriate manner.

When the sensory stimulus output unit 26C is set as the target device, the output control unit 54 outputs, to the sensory stimulus output unit 26C and according to the output specification of the sensory stimulus output unit 26C, a tactile stimulus based on the tactile stimulus data obtained by the content image obtaining unit 52. In that case too, for example, the intensity of the tactile stimulus can be lowered in inverse proportion to the cerebral activation degree of the user U or in proportion to the mental balance degree of the user U. With that, when the user U is focused in some other thing or does not have enough mental space, the risk of being bothered by the tactile stimulus can be lowered. On the other hand, the intensity of the tactile stimulus can be increased in inverse proportion to the cerebral activation degree of the user U or in proportion to the mental balance degree of the user U. With that, the user U becomes able to obtain information from the tactile stimulus in an appropriate manner.

Meanwhile, at Step S12, when it is determined that a danger condition is present and danger notification details are set, the output control unit 54 notifies the target device about the danger notification details so as to ensure that the set output specification is followed.

In this way, the information providing device 10 according to the present embodiment sets the output specification based on the environment information and the biological information, so that a sensory stimulus can be output at an appropriate level according to the environment around the user U and according to the mental state of the user U. Moreover, since the target device to be operated is selected based on the environment information and the biological information, the information providing device 10 becomes able to select an appropriate sensory stimulus according to the environment around the user U or according to the mental state of the user U. However, the information providing device 10 is not limited to use the environment information as well as the biological information. Alternatively, for example, either the environment information or the biological information can be used. Thus, for example, the information providing device 10 either can select the target device based on the environment information and then set the output specification, or can select the target device based on the biological information and then set the output specification.

ADVANTAGEOUS EFFECTS

As explained above, the information providing device 10 according to an aspect of the present embodiment provides information to the user U, and includes the output unit 26, the environment sensor 20, the output specification deciding unit 50, and the output control unit 54. The output unit 26 includes the display unit 26A meant for outputting visual stimuli, the sound output unit 26B meant for outputting auditory stimuli, and the sensory stimulus output unit 26C meant for outputting sensory stimuli other than visual stimuli and auditory stimuli. The environment sensor 20 detects the environment information of the surrounding of the information providing device 10. Based on the environment information, the output specification deciding unit 50 decides on the output specification of visual stimuli, auditory stimuli, and sensory stimuli, that is, decides on the output specification for the display unit 26A, the sound output unit 26B, and the sensory stimulus output unit 26C.

Based on the output specification, the output control unit 54 causes the output unit 26 to output a visual stimulus, an auditory stimulus, and a sensory stimulus. Since the output specification of visual stimuli, auditory stimuli, and sensory stimuli is set based on the environment information, the information providing device 10 can output a visual stimulus, an auditory stimulus, and a sensory stimulus after balancing them out according to the environment around the user U. That enables the information providing device 10 to provide information to the user U in an appropriate manner.

Moreover, the information providing device 10 according to an aspect of the present embodiment includes a plurality of environment sensors meant for detecting mutually different types of environment information, and includes the environment identifying unit 44. Based on the different types of environment information, the environment identifying unit 44 identifies the environment pattern that comprehensively indicates the current environment around the user U. Based on the environment pattern, the output specification deciding unit 50 decides on the output specification. Based on the environment pattern identified from a plurality of types of environment information, the information providing device 10 sets the output specification of the visual stimuli, the auditory stimuli, and the sensory stimuli; and hence becomes able to provide information in a more appropriate manner according to the environment around the user U.

Furthermore, in the information providing device 10 according to an aspect of the present embodiment, as the output specification of a visual stimulus, the output specification deciding unit 50 decides on at least either the size of the image displayed on the display unit 26A, or the degree of transparency of the image displayed on the display unit 26A, or the content (display details) of the image displayed on the display unit 26A. As a result of deciding on such specification as the output specification of a visual stimulus, the information providing device 10 becomes able to provide visual information in a more appropriate manner.

Moreover, in the information providing device 10 according to an aspect of the present embodiment, as the output specification of an auditory stimulus, the output specification deciding unit 50 decides on at least either the sound volume of the sound output from the sound output unit 26B or the acoustic. As a result of deciding on such specification as the output specification of an auditory stimulus, the information providing device 10 becomes able to provide auditory information in a more appropriate manner.

Furthermore, in the information providing device 10 according to an aspect of the present embodiment, the sensory stimulus output unit 26C outputs a tactile stimulus as a sensory stimulus; and, as the output specification of an auditory stimulus, the output specification deciding unit 50 decides on at least either the intensity or the frequency of the tactile stimulus output by the sensory stimulus output unit 26C. As a result of deciding on such specification as the output specification of a tactile stimulus, the information providing device 10 becomes able to provide tactile information in a more appropriate manner.

Moreover, the information providing device 10 according to an aspect of the present embodiment provides information to the user U, and includes the output unit 26, the biological sensor 22, the output specification deciding unit 50, and the output control unit 54. The output unit 26 includes the display unit 26A meant for outputting visual stimuli, the sound output unit 26B meant for outputting auditory stimuli, and the sensory stimulus output unit 26C meant for outputting sensory stimuli other than visual stimuli and auditory stimuli. The biological sensor 22 detects the biological information of the user U. Based on the biological information, the output specification deciding unit 50 decides on the output specification of visual stimuli, auditory stimuli, and sensory stimuli, that is, decides on the output specification for the display unit 26A, the sound output unit 26B, and the sensory stimulus output unit 26C. Based on the output specification, the output control unit 54 causes the output unit 26 to output a visual stimulus, an auditory stimulus, and a sensory stimulus. Since the output specification of visual stimuli, auditory stimuli, and sensory stimuli is set based on the environment information, the information providing device 10 can output a visual stimulus, an auditory stimulus, and a sensory stimulus after balancing them out according to the mental state of the user U. That enables the information providing device 10 to provide information to the user U in an appropriate manner.

Moreover, according to an aspect of the present embodiment, the biological information contains information related to the autonomic nerves of the user U, and the output specification deciding unit 50 decides on the output specification based on the information related to the autonomic nerves of the user U. As a result of setting the output specification of visual stimuli, auditory stimuli, and sensory stimuli based on the information related to the autonomic nerves of the user U, the information providing device 10 can provide information in a more appropriate manner according to the mental state of the user U.

Furthermore, the information providing device 10 according to an aspect of the present embodiment provides information to the user U, and includes the output unit 26, the environment sensor 20, the output specification deciding unit 50, and the output control unit 54. The output unit 26 includes the display unit 26A meant for outputting visual stimuli, the sound output unit 26B meant for outputting auditory stimuli, and the sensory stimulus output unit 26C meant for outputting sensory stimuli other than visual stimuli and auditory stimuli. The environment sensor 20 detects the environment information of the surrounding of the information providing device 10. Based on the environment information, the output selecting unit 48 selects the target device for use from among the display unit 26A, the sound output unit 26B, and the sensory stimulus output unit 26C. The output control unit 54 controls the target device. As a result of selecting the target device based on the environment information, the information providing device 10 becomes able to appropriately select, according to the environment around the user U, a stimulus such as a visual stimulus, an auditory stimulus, or a sensory stimulus. That enables the information providing device 10 to provide information to the user U in an appropriate manner according to the environment around the user U.

Moreover, the information providing device 10 according to an aspect of the present embodiment further includes the biological sensor 22 meant for detecting the biological information of the user; and the output selecting unit 48 selects the target device based on the environment information and based on the biological information of the user U. As a result of selecting the target device, which is to be operated, based on the environment information and the biological information, the information providing device 10 becomes able to select the sensory stimulus in an appropriate manner according to the environment around the user U or according to the mental state of the user U.

Furthermore, according to an aspect of the present embodiment, the environment sensor 20 detects the position information of the information providing device 10 as the environment information; and the biological sensor 22 detects the cerebral activation degree of the user U as the biological information. When at least either the first condition is satisfied in which the position of the information providing device 10 is within a predetermined area and the cerebral activation degree is equal to or smaller than the cerebral activation degree threshold value or the second condition is satisfied in which the variation in the position of the information providing device 10 per unit time is equal to or smaller than a predetermined variation threshold value and in which the cerebral activation degree is equal to or lower than the cerebral activity degree threshold value; the output selecting unit 48 selects the display unit 26A as the target device. On the other hand, when neither the first condition nor the second condition is satisfied, the output selecting unit 48 does not select the display unit 26A as the target device. Thus, whether to operate the display unit 26A is decided in the manner explained above. Hence, for example, when the user U is not in motion and is in a relaxed state or when the user is in a train car in a relaxed state, the information providing device 10 can output a sensory stimulus to the user U in an appropriate manner.

The computer program for performing the information providing method described above may be provided by being stored in a non-transitory computer-readable storage medium, or may be provided via a network such as the Internet. Examples of the computer-readable storage medium include optical discs such as a digital versatile disc (DVD) and a compact disc (CD), and other types of storage devices such as a hard disk and a semiconductor memory.

According to the present disclosure, it becomes possible to provide information to the user in an appropriate manner.

Although the present disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An information providing device that provides information to a user, comprising:
- an output unit including
  - a display unit configured to output a visual stimulus,
  - a sound output unit configured to output an auditory stimulus, and
  - a sensory stimulus output unit configured to output a sensory stimulus other than the visual stimulus and the auditory stimulus;
- an environment sensor configured to detect, as environment information surrounding the information providing device, position information of the information providing device;
- a biological sensor configured to detect, as biological information of the user, cerebral activation degree of the user;
- an output selecting unit configured to select, based on the environment information, one of the display unit, the sound output unit, and the sensory stimulus output unit;
- an output specification deciding unit configured to decide on a reference output specification for adjusting outputs of the display unit, the sound output unit, and the sensory stimulus output unit, based on safety scores that are calculated based on the environment information including the position information of the information providing device; and
- a user state identifying unit configured to calculate an output specification correction degree for correcting the reference output specification in such a way that the output specification is set to be higher in inverse proportion to the cerebral activation degree of the user,
- wherein the output specification deciding unit is configured to correct the reference output specification by applying the output specification correction degree after the reference output specification is determined to calculate the outputs of the display unit, the sound output unit, and the sensory stimulus output unit.

2. The information providing device according to claim 1, wherein the output selecting unit is configured to select, based on the environment information and the biological information of the user, one of the display unit, the sound output unit, and the sensory stimulus output unit.

3. The information providing device according to claim 2, wherein
- when at least one of a first condition in which position of the information providing device is within a predetermined area and the cerebral activation degree is equal to or smaller than a cerebral activation degree threshold value and a second condition in which variation in position of the information providing device per unit time is equal to or smaller than a predetermined variation threshold value and in which the cerebral activation degree is equal to or lower than the cerebral activity degree threshold value is satisfied, the output selecting unit is configured to select the display unit, and
- when neither the first condition nor the second condition is satisfied, the output selecting unit is configured not to select the display unit.

4. The information providing device according to claim 3, wherein the predetermined area is on a railway track or on a road.

5. The information providing device according to claim 1, wherein the sensory stimulus output unit is configured to output a tactile stimulus as the sensory stimulus.

6. The information providing device according to claim 1, wherein
- the output specification deciding unit is configured to decide on, based on the environment information, an output specification of the visual stimulus, the auditory stimulus, and the sensory stimulus, and
- the information providing device further comprises an output control unit configured to cause, based on the output specification, the output unit to output the visual stimulus, the auditory stimulus, and the sensory stimulus.

7. The information providing device according to claim 1, wherein
- the output specification deciding unit is configured to decide on, based on the biological information, an output specification of the visual stimulus, the auditory stimulus, and the sensory stimulus, and
- the information providing device further comprises an output control unit configured to cause, based on the output specification, the output unit to output the visual stimulus, the auditory stimulus, and the sensory stimulus.

8. An information providing method for providing information to a user, comprising:
- detecting, as environment information surrounding an information providing device, position information of the information providing device;
- detecting, as biological information of the user, cerebral activation degree of the user;
- selecting, based on the environment information, one of a display unit configured to output a visual stimulus, a sound output unit configured to output an auditory stimulus, and a sensory stimulus output unit configured to output a sensory stimulus other than the visual stimulus and the auditory stimulus;

deciding on a reference output specification for adjusting outputs of the display unit, the sound output unit, and the sensory stimulus output unit, based on safety scores that are calculated based on the environment information including the position information of the information providing device; and calculating an output specification correction degree for correcting the reference output specification in such a way that the output specification is set to be higher in inverse proportion to the cerebral activation degree of the user, wherein the deciding of the reference output specification includes correcting the reference output specification by applying the output specification correction degree after the reference output specification is determined to calculate the outputs of the display unit, the sound output unit, and the sensory stimulus output unit.

9. A non-transitory computer-readable storage medium storing a computer program for providing information to a user, the computer program causing a computer to execute:

detecting, as environment information surrounding an information providing device, position information of the information providing device;

detecting, as biological information of the user, cerebral activation degree of the user;

selecting, based on the environment information, one of a display unit configured to output a visual stimulus, a sound output unit configured to output an auditory stimulus, and a sensory stimulus output unit configured to output a sensory stimulus other than the visual stimulus and the auditory stimulus;

deciding on a reference output specification for adjusting outputs of the display unit, the sound output unit, and the sensory stimulus output unit, based on safety scores that are calculated based on the environment information including the position information of the information providing device; and calculating an output specification correction degree for correcting the reference output specification in such a way that the output specification is set to be higher in inverse proportion to the cerebral activation degree of the user, wherein the deciding of the reference output specification includes correcting the reference output specification by applying the output specification correction degree after the reference output specification is determined to calculate the outputs of the display unit, the sound output unit, and the sensory stimulus output unit.

10. The information providing device according to claim 1, wherein the output specification deciding unit is configured to decide on, as the output specification of the visual stimulus, at least one of a size of an image to be displayed on the display unit, a degree of transparency of an image to be displayed on the display unit, and details of an image to be displayed on the display unit.

11. The information providing device according to claim 10, wherein the output specification deciding unit is configured to decide on either the size of the image such that a lower the safety score, a smaller the size of the image, or the degree of transparency of the image such that the lower the safety score, a higher the degree of transparency of the image.

12. The information providing device according to claim 1, wherein the output specification deciding unit is configured to decide on, as the output specification of the auditory stimulus, at least one of sound volume and acoustic to be output from the sound output unit.

13. The information providing device according to claim 12, wherein the output specification deciding unit is configured to decide on the sound volume or the acoustic such that a lower the safety score, a higher the sound volume or the extent of the acoustic.

* * * * *